(12) United States Patent
Guignard et al.

(10) Patent No.: US 6,383,746 B1
(45) Date of Patent: May 7, 2002

(54) FUNCTIONAL PROMOTER FOR CCR5

(75) Inventors: Florence Guignard, Bethesda; Philip M. Murphy, Rockville, both of MD (US); Christophe Combadiere, Paris (FR); H. Lee Tiffany, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/177,437

(22) Filed: Oct. 21, 1998

Related U.S. Application Data
(60) Provisional application No. 60/065,934, filed on Oct. 23, 1997.

(51) Int. Cl.[7] .......................... C12Q 1/68; C07H 21/04; C12N 15/00; C12N 15/63
(52) U.S. Cl. ...................... 435/6; 435/69.1; 435/320.1; 536/23.1; 536/24.1; 536/24.3; 536/24.31; 536/24.33; 536/24.5
(58) Field of Search .............................. 536/23.1, 24.1, 536/24.2, 24.5, 24.33; 514/44; 435/325, 375, 6, 320.1

(56) References Cited

U.S. PATENT DOCUMENTS
5,176,996 A * 1/1993 Hogan et al. ............... 435/91.1

FOREIGN PATENT DOCUMENTS
WO  WO 96/39437  12/1996

OTHER PUBLICATIONS

McCombie et al. Human BAC clone 110P12, Advanced Genome Sequence Analysis Course, Cold Spring Harbor Laboratory, NY, Accession No. U95626, May 17, 1997.*

Ausubel et al. Current Protocols in Molecular Biology vol. 1, Section ll, Unit 9.6, Feb. 19, 1997.*
Margolis et al. Molecular Pathogenesis, Modelling, AIDS Pathogenesis Conference, Abstract #349, p. 54, Apr. 8–13, 1997.*
Combadiere et al., "Cloning and functional expression of CC CKR5, a human monocyte CC chemokine receptor selective for MIP-1α, MIP-1β, and RANTES", *Journal of Leukocyte Biology*, vol. 60, Jul. 1996, pp. 147–152.
Carroll et al., "Differential Regulation of HIV–1 Fusion Cofactor Expression by CD28 Costimulation of CD4+ T Cells," *Science*, vol. 276, Apr. 11, 1997, pp. 273–276.
Zimmerman et al., "Inherited Resistance to HIV–1 Conferred by an Inactivating Mutation in CC Chemokine Receptor 5: Studies in Populations with Contrasting Clinical Phenotypes, Defined Racial Background, and Quantified Risk," *Molecular Medicine*, vol. 3, No. 1, Jan. 1997, pp. 23–36.
He et al., "CCR3 and CCR5 are co–receptors for HIV–1 infection of microglia", *Nature*, vol. 385, Feb. 13, 1997, pp. 645–649.
Simmons et al., "Potent Inhibition of HIV–1 Infectivity in Macrophages and Lymphocytes by a Novel CCR5 Antagonist", *Science*, vol. 276, Apr. 11, 1997, pp. 276–279.
Feng Y. et al., *Science*, 272:872–877 (1996).
Combadiere et al., *Journal of Biological Chemistry*, 270:30235 (1995).
Cocchi F. et al., *Science*, 270:1811–1815 (1995).
Gong et al., *Journal of Biological Chemistry*, 271(18):10521–10527 (1996).
Arenzana–Selsdedos et al., "HIV blocked by chemokine antagonist", *Nature*, vol. 383, Oct. 3, 1996, p. 400.

* cited by examiner

*Primary Examiner*—Sean McGarry
*Assistant Examiner*—Janet L. Epps
(74) *Attorney, Agent, or Firm*—Needle & Rosenberg, PC

(57) ABSTRACT

A functional promoter for the chemokine receptor CCR5 is provided. The invention provides a nucleic acid sequence for the promoter and methods of reducing inflammation and susceptibility to HIV infection by suppressing the activity of the promoter.

30 Claims, 4 Drawing Sheets

```
-1006  tctagagccaaggtcacggaagcccagagggcatctgtggctcggagtagctctctgctgtcttctcagctctgctgacaatacttgagattttcaga
       XbaI                                              AP1                                      NF-ATp  NFkB
 -906  tgtcaccaaccaccaagagagcttgatgactgtatatgactgtatatgactgtatatagtcataagaaacctgaacttgaccatatacttatgtcatgtggaaattcat
 -806  agcttcagatagattatatctggagtgaagaatcctgccacctatgtatctggcatagtgtgagtcctcataaatgctactggtttgaagggcaacaaa
                      NFkB                                             AP1
 -706  atagtgaacagagtgaaaatccccactaagatcctgggtccagaaaagatgggaaacctgtttagctcaccgtgagccatagtaaaactctttaga
                         ISRE                                           CTF/NF-1
 -606  caacaggttttttccgtttacagagaacaataatattgggtggtgagcatctgtgtggggttgggtgggataggggagatacggggagagtggagaaaaa
 -506  gggggcacaggtaatgtgaagtccagatcccctacatttaagtgtttaagttggcttaattaatagcaactcttaagataatcagaatt
                                                          CTF/NF-1                      ISRE
 -406  tcttaacctttagcttactgttgaaagccctgtgatctttgtacaaatcatttgctctcttggatagtaatttcttttactaaatgtgggcttttgac
                                                                                 ISRE
 -306  tagatgaatgtaaatgttctttctagctctgatatcctttattctttatatttctaacagattctgtgtgggatgagcagagaacaaaacaaaata
 -206  atccagtgagaaagcccgtaaataaactttcagaccagagatctattctctagcttatttaagctcaacttaaaaggaagaactgttctctgattctt
                                                                                                TATA box
 -106  ttcgccttcaatacacttaatgatttaactccaccctcttcaaaagaaacagcatttcctactttatactgtctatatgattgattgcacagctcat
                                                                   INTRON
   -6  ctggccAGAGAGAGCTGAGACATCGTTCCCCTACAAGAAACTCTCCCGgtaagtaacctctcagctgcttggcctgttagttagcttctgagatgagta
       EXON 1
   95  aaagactttacaggaaaccatagaagacatttggcaaacaccaagtgctcatacacattatctttaaaatataatctttaagataaggaaagggtcacagt
```

FIG.1A 195  ttggaatgagtttcagacgcgttataacatcaagatacaaaacatgattgtgagtgaaagacttaaggggagcaatagtatttttaataactaacaatcc
295  ttacctctcaaagaaagatttgcagagagatgagtcttagctgaaatcttgaaatcttatctttctgctaaggagaactaaccctctccagtgagatgc
395  ctttctgaatatgtgcccacagaagttgtgtctaagtctggttctcttttttttcctccagacaagagggaagctaaaatgtcaaaattaata
495  ttaaattacaaacgccaaataaatttttcctctaatatatcagttcatggcacagttagtatataattctttatgttcaaaattaaaaatgacttt
595  ctagggcttctctcagctgccagtctaaggtgcagggagtttgagactcacagggtttaatagagaaaattctcagctagagcagctgaacttaaat
695  agactaggcaagacagctgtttataagactaaactaccagaatgcatgacattcatctgtggtggcagacgaaacatttttattatattcttgg
795  gtatgtatgacaactcttaattgtgcaactcaaactcaaacacacaaacttcacagaaaatgtgaggatttttacaattggctgtgtcatctatgaccttt
895  ccctggacttggcacccgccatttcactctgactactacatcatgtcaccaaacatctgatgtcttgccttttaattctcttttgaggactgagagg
995  agggtagcatggtagctaagagtgcaggcttcgtgaaaatatttcctgctaattttcgagcaagttactcaccctctctgtgcttc
1095 aagtcctgtgtctgcaaatgtgaaaatgtgcctaaggttgcctaatggcttcatagtgcttagaacagtgattgg
1195 catccagtatgtgccctgagccttcttaattattactggcttgctcatagtcatgttctttgtggctaactctagcgtcaataaaatgttaagact
1295 gagttgcagctgggcatggtggctcatgcctgtaatcccagcattctaggagggctgaggcaggaggatcgcttgagccaggagttcgagaccagctgg
1395 gcaacatagtgtgatctttgtatctatataaaataaacaaatttagcttggtggtgcgcctgtagtcccagccactggaggggtgaggtgagaggat
1495 tgcttgagcccgggatgatcccaggctgcagtgagccagtgatcgtgccactgcactccagcctggggcgacagagtgagaccctgtctcacaacaacag
                                        HindIII
1595 caacaaaaaggctgagctgcaccatgcttgacccagtttcttaaaattgttgtcaaagcttcattcactccatgtgctatagagcacaagatttattt
1695 ggtgagatggtgctttcatgaattcccccaacagagccaagctctccatcagtgacagggaagctagcagcaaccttccctccactacaaacttca
                              EcoRI
1795 ttgcttggccaaaagagagagttaattcaatgtagacatctatgtaggcaattaaaacctattgatgtataaaacagtttgcattcatggagggcaacta
1895 aatacattctaggactttataaagatcacttttatttatgcacag<u>GGTGGAACAAGATG</u>.......
                                          EXON 2  ORF

FIG. 1B

FUNCTIONAL PROMOTER FOR CCR5

This application claims priority from U.S. Provisional Application Ser. No. 60/065,934, filed Oct. 23, 1997, the disclosure of which is incorporated herein by reference.

FIELD OF THE INVENTION

The present invention relates generally to regulatory sequences and more specifically to a nucleic acid sequence for the CCR5 promoter.

BACKGROUND OF THE INVENTION

Chemokines constitute a structurally-related family of secreted proteins, most of which chemoattract and activate specific subsets of leukocytes in vitro. Chemokines are classified into two major subfamilies depending on the position of the first two of four conserved cysteines, which are adjacent in the case of CC chemokines and separated by a single amino acid in the case of CXC chemokines. In vitro, CXC chemokines attract lymphocytes and neutrophils, whereas CC chemokines typically do not attract neutrophils, but instead attract monocytes, macrophages, eosinophils, basophils, dendritic cells and lymphocytes with variable selectivity and potency. In vivo, chemokines appear to act as locally-produced emergency signals that direct leukocytes to sites of infection and tissue injury, but they may also regulate basal leukocyte trafficking, hematopoiesis, angiogenesis and other processes. See, e.g., H. E. Broxmeyer et al., *J Immunol* (1993) 150:3448.

Chemokines activate leukocytes by binding to selective, seven-transmembrane-domain, G protein-coupled receptors present on the plasma membrane. To date, twelve functional human chemokine receptors have been identified: four are specific for CXC chemokines and eight are specific for CC chemokines. Most of the receptors identified so far bind multiple chemokines; conversely, most chemokines tested so far bind to two or more receptor subtypes. In addition to their suspected beneficial role in host defense and tissue repair, several chemokine receptors (CCR2B, CCR3, CCR5 and CXCR4) are exploited pathologically by HIV-1, acting together with CD4 as cell entry coreceptors in vitro (G. Alkhatib et al., *Science* (1996) 272:1955. The HIV-1 strain specificity of the coreceptors is complex. CCR5 is used preferentially by most primary isolates, and not by T cell line-adapted lab strains (Y. Feng et al., *Science* (1996) 272:872; T. Dragic et al., *Nature* (1996) 381:667; H. Deng et al., *Nature* (1996) 381:661; H. Choe et al., *Cell* (1996) 85:1135; B. J. Doranz et al., *Cell* (1996) 85:1149; C. C. Bleul et al., *Nature* (1996) 382:829; E. Oberlin et al., *Nature* (1996) 382:833; L. Zhang et al., *Nature* (1996) 383:768). CXCR4 is used preferentially by lab strains and by some primary isolates. CCR3 is used by both primary isolates and lab-adapted strains. Only a few strains are able to use CCR2B (Doranz et al., supra). The importance of this for HIV-1 transmission in vivo has been clarified for CCR5 by the discovery of a benign, inherited, non-functional mutant CCR5 allele that in homozygous individuals is associated with a high level of resistance to natural HIV-1 infection (M. Samson et al., *Nature* (1996) 382:722). Epidemiologic analysis of the CCR5 $\Delta$32 mutant indicates that it contains a 32 base pair (bp) deletion in the open reading frame (ORF), and encodes a non-functional protein (D. Carrington, et al., *Science* (1996) 273:1856; Y. Huang, et al., *Nat Med* (1996) 2:1240; R. Liu, et al., *Cell* (1996) 86:367; P. A. Zimmerman, et al., *Mol Med* (1997) 3:23). CCR5 $\Delta$32 is relatively common especially in Caucasians where the allele frequency is about 10%. Homozygotes are found in 1% of Caucasian random blood donors but at a much lower than expected frequency in HIV-1+ Caucasians (B. Wang, et al., *Lancet* (1997) 350:9079; M. W. Smith, et al., *Lancet* (1997) 350:9079; T. R. O'Brien, et al., *Lancet* (1997) 349:9060). Moreover, PBMCs from CCR5 D32 homozygotes that have been tested are not injectable in vitro with CCR5-tropic strains of HIV-1 (Liu, et al., supra). CCR5 $\Delta$32 heterozygotes may be partially protected against HIV-1 transmission by heterosexual intercourse, but may be minimally or not at all protected against perinatal transmission or transmission by homosexual intercourse (T. L. Hoffman, et al., *J Infect. Dis.* (1997) 176:1093; R. E. Edelstein, et al., *J. Acquir. Immune. Defic. Syndr Hum. Retrovirol.* (1997) 16:243; C. M. Rousseau, et al., *J. Acquir. Immune. Defic. Syndr. Hum. Retrovirol.* (1997) 16:239). In numerous studies of HIV-1 seroconvertors, progression to AIDS was delayed on average 2 years in CCR5 $\Delta$32 heterozygotes compared to individuals lacking this allele (N. L. Michael, et al., *Nat. Med.* (1997) 3:338). Further, specific agonists for CCR5 (MIP-1$\alpha$, MIP-1$\beta$ and RANTES) are able to suppress infection of CCR5-expressing cells by appropriate HIV-1 strains (F. Cocchi et al., *Science* (1995) 270:1811). Thus, HIV-1+ individuals heterozygous for the mutant CCR5 allele appear to have slightly delayed progression to AIDS compared to individuals homozygous for the wild type allele.

Several other allelic variants of chemokine receptors and one for a chemokine ligand have also been described that affect HIV-1 pathogenesis. m303 is a rare variant of the CCR5 ORF (allele frequency<1%) that encodes a truncated receptor and that protects against HIV-1 infection when found in the compound heterozygous state with CCR5 $\Delta$32. 15,16 Other uncommon variants of the CCR5 ORF have been described but their significance is unknown (M. Carrington, et al., *Am. J. Hum. Genet.* (1 997) 61:126 1; M. A. Ansari-Lari, et al., *Nat Genet* (1997) 16:221).

An allelic variant of the HIV-1 coreceptor CCR2 (named CCR2-64I or 46295-G/A, allele frequency~10%) is associated with delayed progression to AIDS in heterozygotes (L. G. Kostrikis, et al., *Nat Med* (1998) 4:350; M. W. Smith, et al., *Science* (1997) 277:959). This allele has a single base change that causes a conservative substitution in a transmembrane region. CCR2-64I has been linked to a base change in the CCR5 promoter (Kostrikis, et al., supra) however, the functional importance of this has not been defined, and the mechanism of action of CCR2-64I remains unknown. A variant allele of the chemokine SDF-1, which is a ligand for the HIV-1 coreceptor CXCR4, affects the rate of progression to AIDS in homozygous individuals (C. Winkler, et al., *Science* (1998) 279:389). The alteration in this allele is a single base change in the 3'-untranslated region of the SDF-1 mRNA.

CCR5 mRNA has been detected in peripheral blood mononuclear cells (PBMCs) and adherent monocytes. Using a specific monoclonal antibody, CCR5 protein has been detected in microglial cells of the central nervous system and memory T cells. CCR5 protein expression can be upregulated by treatment of T cells with IL-2. In contrast, CCR5 RNA and HIV-1 coreceptor function can be down-regulated in CD4+ T cells by CD3/CD28 costimulation. Thus, measures designed to block CCR5 expression or function could be used to block HIV-1 transmission and/or to treat established HIV-1 infection. In this regard, detailed knowledge of the factors regulating CCR5 expression is an important goal.

SUMMARY OF THE INVENTION

The present invention is based on the identification of the structural organization and sequence of the CCR5 gene and a functional promoter capable of constitutive expression of CCR5 in both myeloid and lymphoid tissues.

One aspect of the invention is an isolated DNA molecule comprising the sequence of the CCR5 promoter and functional regions or portions thereof. Another aspect of the invention is a DNA molecule comprising the sequence of the CCR5 promoter, or a function portion thereof operably linked to a heterologous protein.

Another aspect of the invention is an oligonucleotide or oligonucleotide analog capable of binding to the CCR5 promoter and inhibiting the activity thereof Another aspect of the invention is a method for inhibiting the activity of MIP-1α, MIP-1β, or RANTES by administering an effective amount of a CCR5 promoter-inhibiting oligonucleotide or oligonucleotide analog to a subject in need thereof. Another aspect of the invention is a method for treating or preventing HIV infection in a subject having or at risk of having HIV infection by administering an effective amount of a CCR5 promoter-inhibiting oligonucleotide or oligonucleotide analog to a subject in need thereof. Another aspect of the invention is a method for treating inflammation by administering an effective amount of a CCR5 promoter-inhibiting oligonucleotide or oligonucleotide analog to a subject in need thereof.

Another aspect of the invention is an oligonucleotide agent functional only in myeloid and lymphoid cells, comprising a CCR5 promoter operably linked to an active heterologous protein.

Another aspect of the invention is a method for ablating a selected myeloid or lymphoid cell, by administering an effective amount of an oligonucleotide agent comprising a CCR5 promoter operably linked to a gene encoding a cytotoxic agent.

BRIEF DESCRIPTION OF THE DRAWINGS

FIG. 1 shows the DNA sequence and organization of the CCR5 gene (SEQ ID NO:1). Exon sequence is in capital letters, whereas the intron and the putative promoter region are in lower case. The first nucleotide of exon 1 was chosen as nucleotide +1. The putative TATA box as well as several consensus transcription factor binding sites are also indicated. The last three nucleotides are the first codon of the CCR5 ORF. XbaI, EcoRI and HindIII restriction sites are also indicated. An Alu repeat in the intron is underlined.

DETAILED DESCRIPTION OF THE INVENTION

Figure 2:
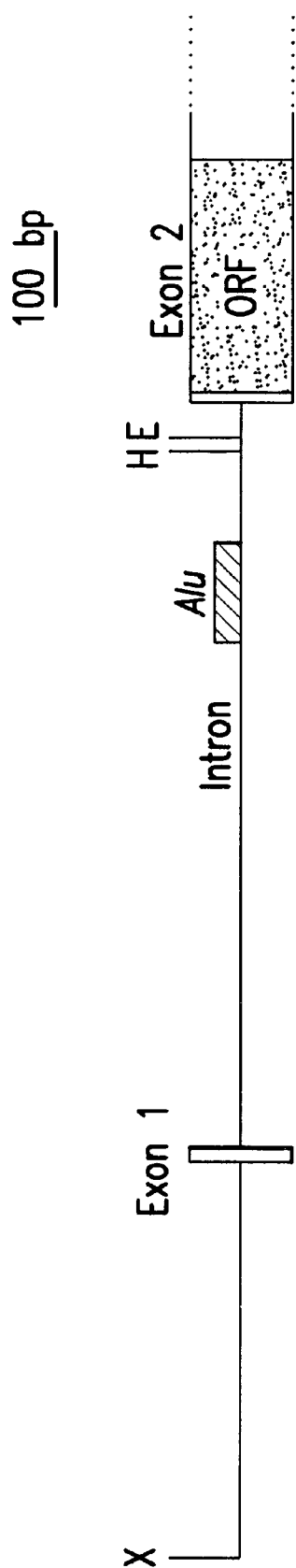
FIG. 2 shows the genomic organization of CCR5. Shaded box, ORF; unshaded box, transcribed but untranslated sequence; hatched box, Alu repeat; X, Xba I; H, Hind III; E, Eco RI. Note that the 3'-limit of exon 2 has not been defined. A length standard is indicated at the upper right.

In an effort to identify nuclear regulatory factors, the present invention provides the location and functional characterization of the CCR5 gene regulatory region, i.e., promoter. The gene consists of two exons separated by a 1.9 kb intron. Exon 1 contains 43 base pairs (bp) of the 5'-untranslated region; exon 2 contains 11 bp of the 5'-untranslated region and the complete open reading frame. Primer extension analysis identified two adjacent transcriptional start points (tsp), which map to the first two bp found in the longest known CCR5 cDNA sequence. A TATA box is present 31 bp upstream from the first tsp. CCR5 mRNA was detected constitutively in both primary human myeloid and lymphoid cells. Consistent with this, transcription of a chloramphenicol acetyl transferase reporter gene was constitutively activated in both transiently transfected myeloid and lymphoid cell lines by the 80 bp gene fragment located immediately upstream of the tsp. Deletion analysis located a strong silencer element between nucleotides −244 and −80, and a strong enhancer element between −486 and −244. These results suggest that the gene region between −486 and −1 may be responsible for constitutive expression of CCR5 in monocyte/macrophages and T lymphocytes.

It must be noted that as used herein and in the appended claims, the singular forms "a", "and", and "the" include plural referents unless the context clearly dictates otherwise. Thus, for example, reference to "a target cell" includes a plurality of such cells and reference to "the transformation vector" includes reference to one or more transformation vectors and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in full for the purpose of describing and disclosing the cell lines, vectors, and methodologies which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Definitions

The term "CCR5 promoter" or "CCR5 regulatory region" as used herein refers to the nucleotide sequence from nucleotide 1 to 486 of SEQ ID NO:1, as well as complementary sequences and sequences which exhibit at least about 75% sequence identity, preferably at least about 85% sequence identity, more preferably at least about 95% sequence identity with the sequence of SEQ ID NO:1. A functional CCR5 promoter is capable of promoting the expression of a gene operably attached thereto in an appropriate cell, such as a myeloid or lymphoid cell. An "isolated" DNA molecule as used herein includes polynucleotides substantially free of other nucleic acids, proteins, lipids, carbohydrates or other materials with which it is naturally associated. Polynucleotide sequences of the invention include DNA, cDNA and RNA sequences which encode the CCR5 promoter. It is understood that all polynucleotides encoding all or a functional portion of the CCR5 promoter are also included herein. Such polynucleotides include naturally occurring, synthetic, and intentionally manipulated polynucleotides. For example, portions of the mRNA sequence may be altered due to alternate RNA splicing patterns or the use of alternate promoters for RNA transcription. As another example, the CCR5 promoter polynucleotide may be subjected to site-directed mutagenesis. The polynucleotide sequence for the CCR5 promoter also includes antisense sequences.

It should be noted that SEQ ID NO:1 includes multiple active domains, for example the promoter domains located between about −486 to −244 upstream of the tsp, and between about −80 to −1 upstream of the tsp. The region from about −244 to −81 upstream of the tsp is believed to contain a suppressor or silencer region.

The terms "MIP-1α" and "MIP-1β" refer to Macrophage Inflammatory Proteins 1α and 1β, respectively. The term RANTES refers to Regulated on Activation, Normal T-cell Expressed and Secreted protein.

The term "cytotoxic agent" refers to a protein or other molecule having the ability to inhibit, kill, or lyse a particular cell. Cytotoxic agents include proteins such as ricin, abrin, diphtheria toxin, or the like. Expression of such proteins intracellularly results in inhibition of protein synthesis or death of the cell.

The term "pathogen protein" refers to a protein specific to or characteristic of a pathogen. Examples of pathogen proteins include, without limitation, hepatitis B virus surface antigen, malaria circumsporozoite antigens, Chlamydia trachomatis major outer membrane protein, HIV gp120, and the like. An agent toxic only in the presence of a pathogen protein is one wherein the agent is relatively inactive in the absence of the pathogen protein, but is activated or metabolized by the pathogen protein to generate a toxic agent. For example, where the pathogen protein is a protease having a unique recognition site for cleavage, an agent toxic only in its presence may be a toxin expressed as a fusion protein having the recognition sequence at the junction between toxin and fusion partner, inactive as a fusion protein, but active upon cleavage.

The term "antisense agent" refers to a molecule which interacts directly with intracellular DNA or RNA to achieve a therapeutic effect. Examples of antisense agents include, without limitation, DNA-binding molecules, triple-helix (or triplex) forming agents, ribozymes, and the like. Antisense agents may be prepared from naturally-occurring nucleotides, or may contain modified bases. An antisense agent is capable of binding to the CCR5 promoter if its binding affinity for a region of the CCR5 promoter is higher than for other, unrelated DNA sequences. Preferably, the antisense agent binds specifically only to the CCR5 promoter.

A "triplex-forming agent" is a molecule which hybridizes to a specific region of duplex DNA, typically lying in the major groove, and inhibits the function of the target DNA by preventing or inhibiting unwinding and/or recognition of the bound sequence. Triplex-forming agents are generally polynucleotides having about 20 to about 40 bases, consisting primarily of G's and T's. Suitable targets for triplex-forming agents are A-G rich regions of sequence, preferably having more than 65% purines on one strand. The most effective triplex-forming agents bind antiparallel to the purine-rich strand, and pair G with G-C pairs, and T with A-T pairs (J. M. Chubb et al., Tibtech (1992) 10:132–36). Triplex-forming agents of the invention are useful for inhibiting the activity of the CCR5 promoter, thus reducing or eliminating expression of CCR5. Exemplary triple-helix forming agents include TGTTTTTGTTTGTTGTTGTG (SEQ ID NO:5); GTGTTGTTGTTTGTTTTTGT (SEQ ID NO:6); TTG-GTTTTGGTGTTTGTTTT (SEQ ID NO:7); TTTTGTTTGTGGTTTTGGTT (SEQ ID NO:8); and a sequence of about 20 to about 38 bases taken from a sequence selected from the group consisting of GTTTTGT-GTGTGGTTTTTTTTGTTTTTGTTGTGTGGTG (SEQ ID NO:9); and GTGGTGTGTTGTTTTTGTTTTTTTTGGT-GTGTGTTTTG (SEQ ID NO:10). These sequences may also be varied by one or two bases, as long as binding affinty is not substantially reduced.

The term "inhibit" or "inhibiting" refers to a measurable reduction in activity, preferably a reduction of at least 10% versus control, more preferably a reduction of 50% or more, still more preferably a reduction of 80% or more. Where there are multiple different activities that may be inhibited (for example, a target protein may have the ability to chemoattract macrophages, and also the ability to cause macrophage proliferation or differentiation), the reduction of any single activity (with or without the other activities) is sufficient to fall within the scope of this definition.

By "transformation" is meant any permanent or transient genetic change induced in a cell following incorporation of new DNA (i.e., DNA exogenous to the cell). The new DNA can be present in the cell as an extrachromosomal or chromosomally integrated element.

By "target cell" is meant a cell(s) that is to be transformed using the methods and compositions of the invention. Transformation may be designed to nonselectively or selectively transform the target cell(s). In general, "target cell" as used herein means a cell that is to be transformed using the method and compositions of the invention.

By "transformed cell" is meant a cell into which (or into an ancestor of which) has been introduced, by means of recombinant DNA techniques, a DNA molecule encoding a molecule (e.g., RNA and/or protein) of interest (e.g., nucleic acid encoding a therapeutic cellular product).

By "nucleotide sequence of interest" or "DNA of interest" is meant any nucleotide sequence (e.g., RNA or DNA sequence) or DNA sequence that encodes a protein or other molecule that is desirable for expression in a target cell (e.g., for production of the protein or other biological molecule (e.g., a therapeutic cellular product) in the target cell). The nucleotide sequence of interest is generally operatively linked to other sequences which are needed for its expression, e.g., a promoter. Use of "DNA of interest" throughout the specification is not meant to limit the invention to deoxyribonucleic acid.

By "gene product of interest" is meant a polypeptide, RNA molecule, or other gene product that is desired for expression in the subject. "Gene products of interest" can include, for example, polypeptides that serve as marker proteins to assess cell transformation and expression, fusion proteins, polypeptides having a desired biological activity, gene products that can complement a genetic defect, RNA molecules, transcription factors, and other gene products that are of interest in regulation and/or expression. "Gene products of interest" can also include nucleotide sequences that provide a desired effect or regulatory function, but do not necessarily encode an RNA molecule or polypeptide per se (e.g., transposons, introns, promoters, enhancers, splice signals, etc.).

By "therapeutic gene product" is meant a polypeptide, RNA molecule or other gene product that, when expressed in a target cell, provides a desired therapeutic effect, e.g., ablation of an infected cell, expression of a polypeptide having a desired biological activity, and/or expression of an RNA molecule for antisense therapy (e.g., regulation of expression of a endogenous or heterologous gene in the target cell genome). For example, Goldsmith et al, WO90/07936, described a system for ablating specific cells within a tissue by using a promoter that is activated only in that tissue to express a therapeutic gene product only in the desired cells. For example, in a patient about to receive a heterologous transplant or graft, one may administer a polynucleotide having a CCR5 promoter operably linked to a gene encoding a toxin. Subsequent activation of the lymphoid or myeloid cells by a pro-inflammatory cytokine would simultaneously induce expression of the toxin, reducing or eliminating the inflammatory response. Acute situations such as transplants may be treated with vectors providing for transient expression (if given at the appropriate times prior to and during treatment), while chronic conditions may be treated with a vector providing for permanent transformation.

By "vector" is meant any compound or formulation, biological or chemical, that facilitates transformation or transfection of a target cell with a DNA of interest. Exemplary biological vectors include viruses, particularly attenuated and/or replication-deficient viruses. Exemplary chemical vectors include lipid complexes and DNA constructs.

By "promoter" is meant a minimal DNA sequence sufficient to direct transcription of a DNA sequence to which it is operably linked. "Promoter" is also meant to encompass those promoter elements sufficient for promoter-dependent gene expression controllable for cell-type specific expression, tissue-specific expression, or inducible by external signals or agents; such elements may be located in the 5' or 3' regions of the native gene.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that the DNA of interest is positioned adjacent a DNA sequence that directs transcription and translation of the introduced DNA (i.e., facilitates the production of, e.g., a polypeptide encoded by a DNA of interest).

By "transgenic organism" is meant a nonhuman organism (e.g., mammal or nonmammal), having a nonendogenous (i.e., heterologous) nucleic acid sequence present as an extrachromosomal element in a portion of its cells or stably integrated into its germ line DNA.

By "transgenic animal" is meant a nonhuman animal subject, usually a mammal, having a nonendogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

As used herein, a "polymorphism" is defined as the existence of a character in two or more variant forms in a population and where the least common form is present in more than 1% of individuals. More specifically, a "genetic polymorphism" is defined as the occurrence in a population of two or more genetically determined variant forms of a particular characteristic at a frequency where the rarest could not be maintained by recurrent mutation alone. For example, a genetic locus is considered to be polymorphic if the variant form (e.g., allele) is found in more than 1% of the population. Further, polymorphisms of DNA segments other than genes also exist and are useful in gene mapping and DNA typing. DNA polymorphisms are due to the addition, deletion, or substitution of a single nucleotide at the site, or to variation in the number of tandem repeats of a DNA sequence.

As used herein, a "restriction fragment length polymorphism" (RFLP) is defined as a DNA polymorphism which results from a loss or creation of a site at which a particular restriction enzyme cuts. DNA carrying the different allelic forms will give different sizes of DNA fragments on digestion with the appropriate restriction enzyme. Polymorphic restriction sites provide useful markers for constructing physical and genetic maps.

As defined herein, a "mutation" is the process whereby changes occur in the quantity or structure of the genetic material of an organism. Mutations are permanent alterations in the genetic material which may led to changes in phenotype. An organism, gene, DNA sequence, etc. in which a mutation has occurred is called a mutant. Mutation can involve modifications of the nucleotide sequence of a single gene, blocks of genes or whole chromosomes. Changes in single genes may be the consequence of point mutations, which involve the removal, addition or substitution of a single nucleotide base within a DNA sequence, or they may be the consequence of changes involving the insertion or deletion of large numbers of nucleotides.

Identification of CCR5 Promoter

Like genes for other chemokine receptors (e.g. CXCR1, CXCR2 and CCR1) and non-chemokine chemoattractant receptors (e.g. the fMet-Leu-Phe receptor and the platelet-activating factor receptor), and unlike most other G protein-coupled receptor genes, the CCR5 gene has a large intron interrupting the 5'-UTR sequence, placing the promoter and transcription start point (tsp) at a considerable genomic distance upstream from the translation initiation site. CXCR2, CCR1 and the fMet-Leu-Phe receptor genes all have two or more introns in the 5'-UTR, and alternative splicing gives rise to multiple mRNA species having the same ORF sequence but different 5'-UTR sequence. This does not appear to be the case for CCR5: variation in length but not in sequence has been found in the 5'-UTR for the two cDNA sequences that have been reported, and a single ~3.5 kb band has been consistently identified by Northern blot analysis of CCR5-expressing cells.

In order to define regions responsible for constitutive CCR5 expression, the activity of a chimeric CAT reporter gene containing 971 bp upstream from exon 1 was tested in various cultured cell lines. This region promoted a high level of constitutive CAT activity, but in the sense orientation only, in both the T cell line Jurkat and the promonocytic cell line U937. Endogenous CCR5 was constitutively expressed in both primary CD4+ and CD8+ T cells and monocytes. Also, a low level of CCR5 mRNA was detected in Jurkat cells by Northern blot analysis.

When a series of deletion mutants of the active 971 bp region upstream from exon 1 was analyzed, an 80 bp region immediately upstream from exon 1 was identified that retained high constitutive promoter activity in the CAT reporter gene system when tested in both Jurkat and U937 cells. Since this region is near the tsp, contains a TATA sequence, and has promoter activity in the CAT reporter gene system, it appears to contain a minimal promoter and may be responsible for constitutive expression of endogenous CCR5 in myeloid and lymphoid cell types.

However, a second region was identified, from −244 to −486 bp relative to the tsp, that also contained high constitutive promoter activity in the CAT reporter gene system when expressed in Jurkat cells. In contrast, the upstream gene regions from −486 to −729 and from −729 to −971 lacked independent promoter activity, and did not significantly affect the constitutive activity of the two downstream promoters. A strong suppressor element must reside between nucleotides −244 to −80, since no promoter activity was observed with a construct between −244 to −1, which contains the 80 bp region that acts as a minimal promoter when tested independently. The activity of this silencer is overcome by the upstream region from −244 to −486, restoring the activity to the level found in the region from −1 to −80 alone.

The transcription factors responsible for constitutive and regulated expression of leukocyte chemoattractant receptors have not yet been defined. The CCR5 promoter region contains several sites with >80% identity with the consensus sequences for elements that bind the transcription factors CTF/NF-1, AP-1, NF-κB and NF-ATp. Also, three ISRE elements were identified suggesting a possible modulation of the promoter activity by interferon. CCR5 expression has been reported to be slowly induced by IL-2 treatment of primary T cells, and downregulated by CD28 activation of PBMCs. However, whether the mechanism involves transcriptional or post-transcriptional regulation, or both, has not yet been defined.

The present invention further provides a foundation for future studies aimed at identifying protein factors and DNA sequences specifically responsible for CCR5 transcription. In addition, the promoter sequence of the present invention can be used to screen cohorts of individuals who have been highly exposed to HIV-1 yet remain uninfected, to test whether additional inactivating CCR5 mutations exist that could confer natural resistance to HIV-1. An analogous precedent for this exists for another chemokine receptor known as the Duffy antigen, which acts pathologically as an erythrocyte-specific cell entry factor for the malaria-causing protozoan *Plasmodium vivax*. An inactivating mutation in a GATA 1 site is present in the Duff promoter of most Africans, and is responsible for natural resistance to vivax malaria. Finally, the CCR5 promoter sequence is a potential target for gene therapy for HIV-1 through triplex DNA and gene targeting strategies.

Vectors and Constructs

Any of a variety of vectors may be used in the present invention. Exemplary biological vectors include viruses, particularly attenuated and/or replication-deficient viruses. Exemplary chemical vectors include lipid complexes and various formulations comprising the nucleotide sequence of interest. The vectors can contain or be derived from any of a variety of viral constructs, bacterial constructs, or constructs capable of replication in eukaryotic and prokaryotic hosts. Preferably, the construct is capable of replication in both eukaryotic and prokaryotic hosts in order to facilitate efficient production of the DNA of interest for use in the method of the invention. Numerous constructs that can replicate in eukaryotic and prokaryotic hosts are known in the art and are commercially available. The construct may be a stably integrating construct or a stable nonintegrating construct. Examples of such constructs include viral constructs and artificial chromosomes (e.g., human artificial chromosomes). The basic vector components include a promoter operably linked to a nucleotide sequence of interest. Additional components of a basic vector include a polyadenylation signal, a splice signal, and terminal repeat sequences (TR), e.g., TR sequences corresponding to the viral sequence from which a viral vector is derived.

Transformation of target cells may be accomplished by administering a DNA- or RNA-liposome complex formulations to the circulatory system. DNA- or RNA-complex formations comprise a mixture of lipids which bind to genetic material (DNA or RNA), providing a hydrophobic coat which allows the genetic material to be delivered into cells. Liposomes which can be used in accordance with the invention include DOPE (dioleyl phosphatidyl ethanol amine), CUDMEDA (N-(5-cholestrum-3-β-ol 3-urethanyl)-N',N'-dimethylethylene diamine). When the DNA of interest is introduced using a liposome, it is preferable to first determine in vitro the optimal values for the DNA:lipid ratios and the absolute concentrations of DNA and lipid as a function of cell death and transformation efficiency. These values can then be used in or extrapolated for use in in vivo transformation. The in vitro determinations of these values can be readily carried out using techniques which are well known in the art.

Other nonviral vectors may also be used in accordance with the present invention. For example, such chemical formulations include DNA or RNA coupled to a carrier molecule (e.g., an antibody or a receptor ligand) which facilitates delivery to host cells for the purpose of altering the biological properties of the host cells. By the term "chemical formulations" is meant modifications of nucleic acids to allow coupling of the nucleic acid compounds to a carrier molecule such as a protein or lipid, or derivative thereof. Exemplary protein carrier molecules include antibodies specific to the cells of a targeted cell or receptor ligands, i.e., molecules capable of interacting with receptors associated with a targeted cell. Alternatively, the DNA of interest may be naked (i.e., not encapsulated), or may be provided as a formulation of DNA and cationic compounds (e.g., dextran sulfate, DEAC-dextran, or poly-L-lysine).

A viral vector may be used in the method of gene therapy of the invention. In general, viral vectors used in accordance with the invention are composed of a viral particle derived from a naturally-occurring virus which has been genetically altered to render the virus replication-defective and to express a recombinant gene of interest. Once the virus delivers its genetic material to a cell, it does not generate additional infectious virus but does introduce exogenous recombinant genes into the cell, preferably into the genome of the cell. Alternatively, the virus containing the DNA of interest is attenuated, i.e. does not cause significant pathology or morbidity in the infected host (i.e., the virus is non-pathogenic or causes only minor disease symptoms). Numerous viral vectors are well known in the art, including, for example, adeno-associated virus (AAV), retrovirus, adenovirus, herpes simplex virus (HSV), cytomegalovirus (CMV), vaccinia and poliovirus vectors. In addition, lentivirus may be used to deliver a DNA of interest to target cells.

Several viral vectors have designed for delivery of nucleotide sequences encoding therapeutic gene products to eukaryotic cells (Cohen-Haguenauer, 1994, *Nouvelle Revue Francaise D Hematologie*, 36 Suppl 1:S3–9). The prototypes for viral mediated gene transfer are the retroviruses (Williams, 1990, *Hum. Gene Therap.*, 1(3):229–39; Merrouche et al., (1992), *Hum. Gene Therap.*, 3:285; Barba et al, (1993), *J. Neurosurg.*, 79:729). Retroviral vectors are characterized by their ability to preferentially integrate into the genome of rapidly dividing cells, making them an ideal vector for introducing tumoricidal factors into proliferating neoplastic cells. Adenoviral vectors infect both dividing and nondividing cells with high efficiency. Adenoviral vectors do not integrate into the genome of the target cell (Berkner, (1992), *Corr. Topics Microbiol. Immunol.*, 158:39; Boviatsis et al., (1994), *Human Gene Therap.*, 5:183) and thus provide temporal recombinant gene expression from an extrachromosomal element for a period of several weeks to a month.

Replication-defective recombinant viruses and plasmid-derived amplicons derived from herpes virus vectors have been developed for gene delivery into cells and tissues (Leib et al., (1993), *Bioessays,* 15:547; Boviatsis et al., (1994), *Human Gene Therap.,* 5:183). Both herpes-derived gene delivery vectors are relatively nonpathogenic to neural tissues and can mediate transgene expression in a substantial number of neurons and other cell types. The recombinant herpes vectors have the distinct advantage that they can enter a latent state in some neuronal cells and thus could potentially mediate stable transgene expression. Adeno-associated virus (AAV) has several desirable characteristics as a vector for gene therapy (Kotin, R. M., (1990), *Proc. Natl. Acad. Sci. USA,* 87:2211; Muzyczka, N., (1992), *Corr. Topics Microbiol. Immunol.,* 158:97). AAV is nonpathogenic in both humans and animals and has a broad host range including human, primate, canine and murine. Its ability to infect and integrate into nondividing cells with high frequency makes it a desirable vector for transfecting quiescent lymphoid or myeloid cells. AAV integration is stable; AAV remained stably integrated in the genome of transformed cells through 150 passages.

Where a viral vector is used to accomplish target cell transformation, the viral vector is preferably a replication-deficient virus. Where a replication-deficient virus is used as the viral vector, infective virus particles containing either DNA or RNA corresponding to the desired therapeutic gene product can be produced by introducing the viral construct into a recombinant cell line which provides the missing components essential for viral replication in trans. Preferably, transformation of the recombinant cell line with the recombinant viral vector will not result in production of replication-competent viruses (e.g., by homologous recombination of the viral sequences of the recombinant cell line into the introduced viral vector).

Methods for production of replication-deficient viral particles containing a nucleotide sequence of interest are well known in the art and are described in, for example, Rosenfeld et al., *Science* 252:431, (1991) and Rosenfeld et al., *Cell* 68:143, (1992) (adenovirus); U.S. Pat. No. 5,139,941 (adeno-associated virus); U.S. Pat. No. 4,861,719 (retrovirus); and U.S. Pat. No. 5,356,806 (vaccinia virus).

The vector for transformation is composed of (in the case of a nonviral vector) or derived from (in the case of recombinant viral vectors) a DNA construct. Preferably, the DNA construct contains a promoter to facilitate expression of the DNA of interest within the target cell. Preferably the promoter is a strong, eukaryotic promoter. Exemplary eukaryotic promoters include promoters from cytomegalovirus (CMV), mouse mammary tumor virus (MMTV), Rous sarcoma virus (RSV), adenovirus, herpes simplex virus (HSV) (e.g., HSV thyrnidine kinase promoter), and SV40. More specifically, exemplary promoters include the Ad 2 major late promoter (Wong et al. 1986 *J. Virol.* 60(1) :149–56), the promoter from the immediate early gene of human CMV (Boshart et al., *Cell* 41:521–530, 1985) and the promoter from the long terminal repeat (LTR) of RSV (Gorman et al. 1982 *Proc. Natl. Acad. Sci. USA* 70:6777–6781). Of these promoters, the CMV and Ad 2 major late promoters are especially preferred.

Other components of constructs suitable for use include a marker(s) (e.g., an antibiotic resistance gene (such as an ampicillin resistance gene), β-galactosidase or green fluorescent protein (GFP)) to aid in selection of cells containing the construct, an origin of replication for stable replication of the construct in a bacterial cell (preferably, a high copy number origin of replication), a nuclear localization signal, or other elements which facilitate production of the DNA construct, the protein encoded thereby, or both.

For eukaryotic expression, the construct should contain at a minimum a eukaryotic promoter operably linked to the DNA of interest, which is in turn operably linked to a polyadenylation sequence. The polyadenylation signal sequence may be selected from any of a variety of polyadenylation signal sequences known in the art. Preferably, the polyadenylation signal sequences are the polyadenylation signal sequences of the SV40 late and/or early genes. The construct may also include one or more introns, which can increase levels of expression of the DNA of interest. Any of a variety of introns known in the art may be used. For example, the human β-globin intron can be inserted in the construct at a position 5' to the DNA of interest to provide enhanced expression.

The DNA of interest can be inserted into a construct so that the therapeutic protein is expressed as a fusion protein. For example, the therapeutic protein can be a portion of a fusion protein having β-galactosidase or a portion thereof at the N-terminus and the therapeutic protein at the C-terminal portion. Or, for example, the therapeutic protein (or a portion thereof) can be fused to green fluorescent protein (or a portion thereof). Methods for production of such fusion proteins are well known in the art (see, for example, Sambrook et al. *Molecular Cloning: A Laboratory Manual,* 2nd Ed., 1989, Cold Spring Harbor Laboratory Press, Cold Spring Harbor, N.Y.; Kain et al. 1995 *Biotechniques* 19:650–655; and Clontech Laboratories, Inc., *Technical Service Protocol* #PT2040-1, Version #PR64559, each of which are hereby incorporated by reference with respect to methods and compositions for production and expression of fusion proteins). Production of a fusion protein can facilitate monitoring of therapy, e.g., through detection of the fusion protein from a sample of peripheral blood.

It may also be desirable to produce altered forms of the therapeutic proteins that are, for example, protease resistant or have enhanced activity relative to the wild-type protein. Further, where the therapeutic protein is a hormone, it may be desirable to alter the protein's ability to form dimers or multimeric complexes.

The construct containing the DNA of interest can also be designed so as to provide for site-specific integration into the genome of the target cell. Methods and compositions for preparation of such site-specific constructs are described in, for example, U.S. Pat. No. 5,292,662, incorporated herein by reference with respect to the construction and use of such site-specific insertion vectors. Techniques for production of nucleic acid constructs for expression of exogenous DNA or RNA sequences in a host are known in the art (see, for example, Kormal et al., *Proc. Natl. Acad. Sci. USA,* 84:2150–2154, 1987; and Sambrook et al., supra, each of which are hereby incorporated by reference with respect to methods and compositions for eukaryotic expression of a DNA of interest).

Transformation and Administration

In general, transformation is accomplished by introducing the nucleotide sequence of interest (e.g., the DNA of interest contained in a construct that is formulated in a chemical vector solution or as a viral vector) directly into the circulatory system. Introduction of the DNA of interest can be accomplished by any means, generally by injection or infusion. In one embodiment, the DNA of interest is delivered to the bloodstream in vivo by infusion, preferably using an osmotic minipump. Implantation of an osmotic minipump and its use in the delivery of pharmacologic agents to the brain, kidney, and guinea pig cochlea have been described (Schindler et al., 1977 *Arch. Otolaryngol,* 103:691–699; Nau, 1985 *Toxical. Appl. Pharmacol.,* 80:243–250; Sendelbeck et al., 1985 *Brain Res.,* 328:251–258; Ruers et al., 1986 *Transplantation,* 41:156–161; Davies et al., 1994 *Am. J. Otology,* 15:757–761, Schindler et al., 1995 *Am. J. Otology,* 16:304–309; and Shah et al., 1995 *Am. J. Otology,* 16:310–314, each of which are incorporated herein by reference with respect to the description of the implantation and use of such osmotic minipumps).

The form of the preparation for administration will depend upon several factors such as the cell targeted for gene transfer and whether a biological or nonbiological vector is employed. The vector solution can also contain therapeutic compounds (e.g, nerve growth factors, anti-inflammatory agents, antibiotic agents) in addition to the DNA of interest, as well as compounds to adjust, for example, the pH, osmolarity, and/or viscosity of the vector solution. The preparation can additionally contain compounds that facilitate entry of the agent into cells such as lipofectin, permeability-enhancing agents (e.g., detergents), or other transformation-enhancing agents. Where the vector is a viral vector, the preparation can also include a co-infecting virus to facilitate infection and transformation. Where the DNA of interest is administered in a recombinant viral vector, e.g., an AAV vector, the vector solution is preferably normal saline.

The amount of DNA and/or number of viral particles administered will vary greatly according to a number of factors including the susceptibility of the target cells to transformation, subject-dependent variables such as age, weight, sensitivity or responsiveness to therapy, the levels of protein expression desired, and the condition to be treated. For example, where a recombinant AAV vector is used, the total delivered viral dosage can be in the range of 1 virus per 5 target cells, preferably 1 virus per 10 target cells, more preferably 1 virus per 20 target cells or less. Generally, the amounts of DNA for transformation of human target cells can be extrapolated from the amounts of DNA effective for gene therapy in an animal model.

The amount of DNA and/or viral particles necessary to accomplish transformation of the target cells will decrease with an increase in the efficiency of the transformation method used. In general, the amount of DNA and/or the number of infectious viral particles is an amount effective to infect the targeted cells or structure, transform a sufficient number of cells, and provide for expression of desired or therapeutic levels of the protein or other gene product. Where transformation is transient (e.g., the DNA of interest is maintained for some period as an extrachromosomal element), the time period over which expression is desired may also be taken into consideration. The desired number of copies (e.g., copy number) of the DNA of interest in the cell may additionally be taken into account in determining the amount of DNA and/or number of viral particles to be delivered to the subject, and such may be adjusted as desired to, for example, achieve varying levels of gene product expression.

Transformation can be accomplished such that expression of the gene product of interest is either transient, inducible, or stable. For example, where the DNA of interest is present in the transformed cell as an extrachromosomal element (e.g., as with AAV vectors), expression of the gene product is generally transient. Inducible expression can be achieved so that expression of the gene product of interest is induced only in the presence of some signal that is, for example, specific to a certain type of cell(e.g., is only expressed in HIV-infected myeloid cells or a specific type of myeloid or lymphoid cell due to the presence of a cell-specific or tissue-specific transcription factor in the transformed cell).

Alternatively, gene product can be inducible by the presence of an extracellular factor that can be introduced at the same time as the transforming vector solution is introduced into the circulation, and/or subsequent to target cell transformation. Stable expression of the gene product can be achieved by, for example, introduction of the DNA of interest in a vector to provide for stable genomic integration into the target cell and expression of the gene product from the DNA of interest via a constitutive promoter.

Where expression of the gene product of interest is transient, expression can be maintained in the target cell for a period ranging from several days to several months or years, e.g., for 6 months to 1 year, for 4 months to 6 months, for 2 weeks to 8 weeks, or for as little as one week or a few days (e.g., 3 to 5 days, or 1 to 3 days). Transient expression of the gene product of interest may be desirable where the subject is being exposed to the therapeutic regimen for the first time (e.g., where it is desirable to monitor the responsiveness and/or sensitivity of the subject), or where expression is desired only over a specific period (e.g., for a period after transplantation without permanent expression, or for a period during a specific stage of development). The period of transient expression can be adjusted by, for example, adjusting the transformation protocol to achieve a desired number of transformed cells or, where a viral vector is used, by adjusting aspects of the vector associated with maintenance in a cell (e.g., replication functions or other functions associated with vector stability and/or copy number).

The actual amounts of DNA and/or number of infectious viral particles required can be readily determined based upon such factors as the levels of protein expression achieved in cell lines in vitro, and the susceptibility of the target cells to transformation.

Methods of Treatment

Based on the description above, the invention further provides a method for inhibiting the activity of MIP-1α, MIP-1β, or RANTES in a population of cells containing myeloid or lymphoid cells by providing a CCR5 promoter antisense or triplex agent capable of binding to a CCR5 promoter; and administering to myeloid or lymphoid cells an effective amount of CCR5 promoter antisense agent. The method of the invention can be in vivo or ex vivo, for example.

The invention also provides a method for treating inflammation in a subject by providing a CCR5 promoter antisense agent capable of binding to a CCR5 promoter; and administering to the subject an effective amount of CCR5 promoter antisense agent. The method for treating and preventing diseases involving an inflammatory response, includes diseases such as asthma, arthritis, Crohn's disease, lupus, Grave's disease, and pulmonary disease associated with cystic fibrosis.

In another embodiment, the invention provides a method for treating or preventing HIV infection in a subject having or at risk of having an HIV infection including providing a CCR5 promoter antisense agent capable of binding to a CCR5 promoter; and administering to the subject an effective amount of CCR5 promoter antisense agent.

Antisense technology offers a very specific and potent means of inhibiting HIV infection of cells that contain CCR5 and CCR5 promoter, for example, by decreasing the amount of CCR5 expression in a cell. Antisense polynucleotides in context of the present invention includes both short sequences of DNA known as oligonucleotides of usually 10–50 bases in length as well as longer sequences of DNA that may exceed the length of the CCR5 promoter sequence itself. Antisense polynucleotides useful for the present invention are complementary to specific regions of the CCR5 promoter region. Hybridization of antisense polynucleotides to their target transcripts can be highly specific as a result of complementary base pairing. The capability of antisense polynucleotides to hybridize is affected by such parameters as length, chemical modification and secondary structure of the transcript which can influence polynucleotide access to the target site. See Stein et al, *Cancer Research* 48:2659 (1988). An antisense polynucleotide can be introduced to a cell by introducing a DNA segment that codes for the polynucleotide into the cell such that the polynucleotide is made inside the cell. An antisense polynucleotide can also be introduced to a cell by adding the polynucleotide to the environment of the cell such that the cell can take up the polynucleotide directly. The latter route is preferred for the shorter polynucleotides of up to about 20 bases in length.

In selecting the preferred length for a given polynucleotide, a balance must be struck to gain the most favorable characteristics. Shorter polynucleotides such as 10- to 15-mers, while offering higher cell penetration, have lower gene specificity. In contrast, while longer polynucleotides of 20–30 bases offer better specificity, they show decreased uptake kinetics into cells. See Stein et al., Phosphorothioate Oligodeoxynucleotide Analogues in "Oligodeoxynucleotides—Antisense Inhibitors of Gene Expression" Cohen, ed. McMillan Press, London (1988). Accessibility to mRNA target sequences also is of importance and, therefore, loop-forming regions in targeted mRNAs offer promising targets. In this disclosure the term "polynucleotide" encompasses both oligomeric nucleic acid moieties of the type found in nature, such as the deoxyribonucleotide and ribonucleotide structures of DNA and RNA, and man-made analogues which are capable of binding to nucleic acids found in nature. The polynucleotides of the present invention can be based upon ribonucleotide or deoxyribonucleotide monomers linked by phosphodiester bonds, or by analogues linked by methyl phosphonate, phosphorothioate, or other bonds. They may also comprise monomer moieties which have altered base structures or other modifications, but which still retain the ability to bind to naturally occurring DNA and RNA structures. Such polynucleotides may be prepared by methods well-known in the art, for instance using commercially available machines and reagents available from Perkin-Elmer/Applied Biosystems (Foster City, Calif.).

Phosphodiester-linked polynucleotides are particularly susceptible to the action of nucleases in serum or inside cells, and therefore in a preferred embodiment the antisense or triplex polynucleotides of the present invention are phosphorothioate or methyl phosphonate-linked analogues, which have been shown to be nuclease-resistant. Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar ("backbone") linkages. Most preferred are phosphorothioates and those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Also preferred are oligonucleotides having morpholino backbone structures. Summerton, J. E. and Weller, D. D., U.S. Pat. No. 5,034,506. In other preferred embodiments, such as the protein-nucleic acid or peptide-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O.

Buchardt, *Science*, 1991, 254, 1497. Other preferred oligonucleotides may contain alkyl and halogen-substituted sugar moieties comprising one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S— or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a cholesteryl group; a conjugate; a reporter group; an interealator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group. Other preferred embodiments may include at least one modified base form or "universal base" such as inosine.

The preparation of base-modified nucleosides, and the synthesis of modified oligonucleotides using said base-modified nucleosides as precursors, has been described, for example, in U.S. Pat. Nos. 4,948,882 and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (e.g., U.S. Pat. No. 5,118,802) and can be used similarly.

Persons of ordinary skill in this art will be able to select other linkages for use in the invention. These modifications also may be designed to improve the cellular uptake and stability of the polynucleotides.

In another embodiment of the invention, the antisense polynucleotide is an RNA molecule produced by introducing an expression construct into the target cell. The RNA molecule thus produced is chosen to have the capability to hybridize to CCR5 regulatory region. Such molecules that have this capability can inhibit translation of the CCR5 mRNA by binding to the regulatory region (e.g., promoter) and thereby inhibit the ability of HIV to infect cells that contain the RNA molecule.

The polynucleotides which have the capability to hybridize with mRNA targets can inhibit expression of corresponding gene products by multiple mechanisms. In "translation arrest," the interaction of polynucleotides with target mRNA blocks the action of the ribosomal complex and, hence, prevents translation of the messenger RNA into protein. Haeuptle et al., *Nucl. Acids. Res.* 14:1427 (1986). In the case of phosphodiester or phosphorothioate DNA polynucleotides, intracellular RNase H can digest the targeted RNA sequence once it has hybridized to the DNA oligomer. Walder and Walder, *Proc. Natl. Acad. Sci. USA* 85:5011 (1988). As a further mechanism of action, in "transcription arrest" it appears that some polynucleotides can form "triplex," or triple-helical structures with double stranded genomic DNA containing the gene of interest, e.g., the CCR5 regulatory region, thus interfering with transcription by RNA polymerase. Giovannangeli et al., *Proc. Natl. Acad. Sci.* 90:10013 (1993); Ebbinghaus et al. *J. Clin. Invest.* 92:2433 (1993).

In one preferred embodiment, CCR5 polynucleotides are synthesized according to standard methodology. Phosphorothioate modified DNA polynucleotides typically are synthesized on automated DNA synthesizers available from a variety of manufacturers. These instruments are capable of synthesizing nanomole amounts of polynucleotides as long as 100 nucleotides. Shorter polynucleotides synthesized by modern instruments are often suitable for use without further purification. If necessary, polynucleotides may be purified by polyacrylamide gel electrophoresis or reverse phase chromatography. See Sambrook et al., *Molecular Cloning: A Laboratory Manual,* Vol. 2, Chapter 11, Cold Spring Harbor Laboratory Press, Cold Spring Harbor, N.Y. (1989).

Alternatively, a CCR5 polynucleotide in the form of antisense RNA or triplex agent may be introduced to a cell by its expression within the cell from a standard DNA expression vector. CCR5 antisense or triplex sequences can be cloned from standard plasmids into expression vectors, which expression vectors have characteristics permitting higher levels of, or more efficient expression of the resident polynucleotides. At a minimum, these constructs require a prokaryotic or eukaryotic promoter sequence which initiates transcription of the inserted DNA sequences. A preferred expression vector is one where the expression is inducible to high levels. This is accomplished by the addition of a regulatory region which provides increased transcription of downstream sequences in the appropriate host cell. See Sambrook et al., Vol. 3, Chapter 16 (1989).

For example, CCR5 antisense or triplex expression vectors can be constructed using the polymerase chain reaction (PCR) to amplify appropriate fragments from single-stranded cDNA of a plasmid such as pRc in which CCR5 promoter region has been incorporated. Fang et al., *J. Biol. Chem.* 267 25889–25897 (1992). Polynucleotide synthesis and purification techniques are described in Sambrook et al. and Ausubel et al. (eds.), Current Protocols in Molecular Biology (Wiley Interscience 1987) (hereafter "Ausubel"), respectively. The PCR procedure is performed via well-known methodology. See, for example, Ausubel, and Bangham, "The Polymerase Chain Reaction: Getting Started," in Protocols in Human Molecular Genetics (Humana Press 1991). Moreover, PCR kits can be purchased from companies such as Stratagene Cloning Systems (La Jolla, Calif.) and Invitrogen (San Diego, Calif.).

The products of PCR are subcloned into cloning vectors. In this context, a "cloning vector" is a DNA molecule, such as a plasmid, cosmid or bacteriophage, that can replicate autonomously in a host prokaryotic cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Suitable cloning vectors are described by Sambrook et al., Ausubel, and Brown (ed.), Molecular Biology Labfax (Academic Press 1991). Cloning vectors can be obtained, for example, from Gibco/Brl (Gaithersburg, Md.), Clontech Laboratories, Inc. (Palo Alto, Calif.), Promega Corporation (Madison, Wis.), Stratagene Cloning Systems (La Jolla, Calif.), Invitrogen (San Diego, Calif.), and the American Type Culture Collection (Rockville, Md.).

The PCR products can be ligated into a "TA" cloning vector for example. Methods for generating PCR products with a thymidine or adenine overhang are well-known to those of skill in the art. See, for example, Ausubel at pages 15.7.1–15.7.6. Moreover, kits for performing TA cloning can be purchased from companies such as Invitrogen (San Diego, Calif.).

Cloned antisense or triplex fragments are amplified by transforming competent bacterial cells with a cloning vector and growing the bacterial host cells in the presence of the appropriate antibiotic. See, for example, Sambrook et al., and Ausubel. PCR is then used to screen bacterial host cells for CCR5 antisense orientation clones. The use of PCR for bacterial host cells is described, for example, by Hofmann et al., "Sequencing DNA Amplified Directly from a Bacterial Colony," in PCR Protocols: Methods and Applications, White (ed.), pages 205–210 (Humana Press 1993), and by Cooper et al., "PCR-Based Full-Length cDNA Cloning Utilizing the Universal-Adaptor/Specific DOS Primer-Pair Strategy," Id. at pages 305–316.

Cloned antisense fragments are cleaved from the cloning vector and inserted into an expression vector. For example, HindIII and XbaI can be used to cleave the antisense fragment from TA cloning vector pCR™-II (Invitrogen;San Diego, Calif.). Suitable expression vectors typically contain (1) prokaryotic DNA elements coding for a bacterial origin of replication and an antibiotic resistance marker to provide for the amplification and selection of the expression vector in a bacterial host; (2) DNA elements that control initiation of transcription, such as a promoter; and (3) DNA elements that control the processing of transcripts, such as a transcription termination/polyadenylation sequence.

For a mammalian host, the transcriptional and translational regulatory signals preferably are derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1: 273 (1982)); the TK promoter of Herpes virus (McKnight, *Cell* 31: 355 (1982)); the SV40 early promoter (Benoist et al., *Nature* 290: 304 (1981); the Rous sarcoma virus promoter (Gorman et al., *Proc. Nat'l Acad. Sci. USA* 79: 6777 (1982)); and the cytomegalovirus promoter (Foecking et al, *Gene* 45: 101 (1980)).

Alternatively, a prokaryotic promoter, such as the bacteriophage T3 RNA polymerase promoter, can be used to control fusion gene expression if the prokaryotic promoter is regulated by a eukaryotic promoter. Zhou et al., *Mol. Cell. Biol.* 10: 4529 (1990); Kaufman et al., *Nucl. Acids Res.* 19: 4485 (1991).

A vector for introducing at least one antisense polynucleotide into a cell by expression from a DNA is the vector pRc/CMV (Invitrogen (San Diego, Calif.), which provides a high level of constitutive transcription from mammalian enhancer-promoter sequences. Cloned CCR5 antisense or triplex vectors are amplified in bacterial host cells, isolated from the cells, and analyzed as described above.

Another possible method by which antisense sequences may be exploited is via gene therapy. Virus-like vectors, usually derived from retroviruses, may prove useful as vehicles for the importation and expression of antisense constructs in human cells. Generally, such vectors are non-replicative in vivo, precluding any unintended infection of non-target cells. In such cases, helper cell lines are provided which supply the missing replicative functions in vitro, thereby permitting amplification and packaging of the antisense vector. A further precaution against accidental infection of non-target cells involves the use of target cell-specific regulatory sequences. When under the control of such sequences, antisense or triplex constructs would not be expressed in normal tissues.

Two prior studies have explored the feasibility of using antisense polynucleotides to inhibit the expression of a heparin binding growth factor. Kouhara et al., *Oncogene* 9: 455–462 (1994); Morrison, *J. Biol. Chem.* 266: 728 (1991). Kouhara et al. showed that androgen-dependent growth of mouse mammary carcinoma cells (SC-3) is mediated through induction of androgen-induced, heparin binding growth factor (AIGF). An antisense 15-mer corresponding to the translation initiation site of AIGF was measured for its ability to interfere with androgen-induction of SC-3 cells. At concentrations of 5 $\mu$M, the antisense polynucleotide effectively inhibited androgen-induced DNA synthesis. Morrison showed that antisense polynucleotides targeted against basic fibroblast growth factor can inhibit growth of astrocytes in culture. Thus, the general feasibility of targeting an individual gene product in a mammalian cell has been established.

Antisense polynucleotides according to the present invention are derived from any portion of the CCR5 regulatory region. Based upon the size of the human genome, statistical studies show that a DNA segment approximately 14–15 base pairs long will have a unique sequence in the genome. To ensure specificity of targeting CCR5 RNA, therefore, it is preferred that the antisense polynucleotides are at least 15 nucleotides in length. Thus, the shortest polynucleotides contemplated by the present invention encompass nucleotides corresponding to positions −1 to −14, −1 to −15, −1 to −16, −1 to −17, −1 to −18, −1 to −19, −2 to −16, −3 to −17, etc. of the CCR5 cDNA sequence. Position 1 refers to the first nucleotide of the CCR5 coding region.

Not every polynucleotide will provide a sufficient degree of inhibition or a sufficient level of specificity for the CCR5 target. Thus, it will be necessary to screen polynucleotides to determine which have the proper antisense or triplex characteristics. A preferred method to assay for a useful antisense or triplex polynucleotide is the inhibition of cell fusion between: (1) cells that contain CD4 and CCR5; and (2) cells that contain env.

Administration of polynucleotides to a subject, either as a naked, synthetic polynucleotide or as part of an expression vector, can be effected via any common route (oral, nasal, buccal, rectal, vaginal, or topical), or by subcutaneous, intramuscular, intraperitoneal, or intravenous injection. Pharmaceutical compositions of the present invention, however, are advantageously administered in the form of injectable compositions. A typical composition for such purpose comprises a pharmaceutically acceptable solvent or diluent and other suitable, physiologic compounds. For instance, the composition may contain polynucleotide and about 10 mg of human serum albumin per milliliter of a phosphate buffer containing NaCl.

As much as 700 milligrams of antisense polynucleotide has been administered intravenously to a patient over a course of 10 days (ie., 0.05 mg/kg/hour) without signs of toxicity. Sterling, "Systemic Antisense Treatment Reported," *Genetic Engineering News* 12: 1, 28 (1992).

Other pharmaceutically acceptable excipients include non-aqueous or aqueous solutions and non-toxic compositions including salts, preservatives, buffers and the like. Examples of non-aqueous solutions are propylene glycol, polyethylene glycol, vegetable oil and injectable organic esters such as ethyloleate. Aqueous solutions include water, alcoholic/aqueous solutions, saline solutions, parenteral vehicles such as sodium chloride, Ringer's dextrose, etc. Intravenous vehicles include fluid and nutrient replenishers. Preservatives include antimicrobial, anti-oxidants, chelating agents and inert gases. The pH and exact concentration of the various components the pharmaceutical composition are adjusted according to routine skills in the art. A preferred pharmaceutical composition for topical administration is a dermal cream or transdermal patch.

Antisense or triplex polynucleotides or their expression vectors may be administered by injection as an oily suspension. Suitable lipophilic solvents or vehicles include fatty oils, such as sesame oil, or synthetic fatty acid esters, such as ethyl oleate or triglycerides. Moreover, antisense polynucleotides or vectors may be combined with a lipophilic carrier such as any one of a number of sterols including cholesterol, cholate and deoxycholic acid. A preferred sterol is cholesterol. Aqueous irjection suspensions may contain substances which increase the viscosity of the suspension include, for example, sodium carboxymethyl cellulose, sorbitol, and/or dextran. Optionally, the suspension also contains stabilizers.

An alternative formulation for the administration of antisense or triplex CCR5 polynucleotides involves liposomes. Liposome encapsulation provides an alternative formulation for the administration of CCR5 polynucleotides and expression vectors. Liposomes are microscopic vesicles that consist of one or more lipid bilayers surrounding aqueous compartments. See, generally, Bakker-Woudenberg et al., *Eur. J. Clin. Microbiol. Infect. Dis.* 12 (Suppl. 1): S61 (1993), and Kim, *Drugs* 46: 618 (1993). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 $\mu$m to greater than 10 $\mu$m. A variety of agents can be encapsulated in liposomes: hydrophobic agents partition in the bilayers and hydrophilic agents partition within the inner aqueous space(s). See, for example, Machy et al., Liposomes in Cell Biology and Pharmacology (John Libbey 1987), and Ostro et al., *American J. Hosp. Pharm.* 46: 1576 (1989). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents. Scherphof et al., *Ann. N.Y. Acad. Sci.* 446: 368 (1985).

After intravenous administration, conventional liposomes are preferentially phagocytosed into the reticuloendothelial system. However, the reticuloendothelial system can be circumvented by several methods including saturation with large doses of liposome particles, or selective macrophage inactivation by pharmacological means. Claassen et al., *Biochim. Biophys. Acta* 802: 428 (1984). In addition, incorporation of glycolipid- or polyethelene glycol-derivatised phospholipids into liposome membranes has been shown to result in a significantly reduced uptake by the reticuloendothelial system. Allen et al., *Biochim. Biophys. Acta* 1068: 133 (1991); Allen et al., *Biochim. Biohys. Acta* 1150: 9 (1993) These Stealth® liposomes have an increased circulation time and an improved targeting to tumors in animals. Woodle et al., *Proc. Amer. Assoc. Cancer Res.* 33: 2672

(1992). Human clinical trials are in progress, including Phase III clinical trials against Kaposi's sarcoma. Gregoriadis et al., *Drugs* 45: 15 (1993).

Antisense or triplex polynucleotides and expression vectors can be encapsulated within liposomes using standard techniques. A variety of different liposome compositions and methods for synthesis are known to those of skill in the art. See, for example, U.S. Pat. Nos. 4,844,904, 5,000,959, 4,863,740, and 4,975,282, all of which are hereby incorporated by reference.

Liposomes can be prepared for targeting to particular cells or organs by varying phospholipid composition or by inserting receptors or ligands into the liposomes. For instance, antibodies specific to tumor associated antigens may be incorporated into liposomes, together with antisense polynucleotides or expression vectors, to target the liposome more effectively to the tumor cells. See, for example, Zelphati et al., *Antisense Research and Development* 3: 323–338 (1993), describing the use "immunoliposomes" containing antisense polynucleotides for human therapy.

In general, the dosage of administered liposome-encapsulated antisense polynucleotides and vectors will vary depending upon such factors as the patient's age, weight, height, sex, general medical condition and previous medical history. Dose ranges for particular formulations can be determined by using a suitable animal model.

The above approaches can also be used not only with antisense nucleic acid, but also with ribozymes, or triplex agents to block transcription or translation of a specific CCR5 regulatory region.

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med. Assn.*, 260:3030, 1988). A major advantage of this approach is that, because they are sequence-specific, only mRNAs with particular sequences are inactivated.

Identification of CCR5 Suppressive Agents

The invention also provides a method for identifying a composition that suppresses the expression of CCR5. The method includes incubating components comprising the composition and a nucleic acid sequence comprising a functional portion of the CCR5 promoter of SEQ ID NO:1, or polymorphisms thereof, operably linked to a detectable reporter under conditions sufficient to allow the components to interact; and identifying a composition which suppresses CCR5 promoter activity by detecting the reporter. The composition or compound may be provided as a library of candidate compounds. The reporter may include those described herein, such as CAT or GFP, or other common reporters known to those of skill in the art.

Incubating includes conditions which allow contact between the test composition and CCR5 promoter (SEQ ID NO:1) or functional fragments thereof as described herein. Contacting includes in solution and in solid phase. The test compound or composition may optionally be a combinatorial library for screening a plurality of compositions. Compositions identified in the method of the invention can be further evaluated, detected, cloned, sequenced, and the like, either in solution or after binding to a solid support, by any method usually applied to the detection of a specific DNA sequence such as PCR, oligomer restriction (Saiki, el al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

Expression of the reporter or exogenous gene operably linked to SEQ ID NO:1 can be monitored by a functional assay or assay for a protein product, for example. The exogenous gene is therefore a gene which will provide an assayable or measurable expression product in order to allow detection of expression of the exogenous gene. Such exogenous genes include, but are not limited to, reporter genes such as chloramphenicol a-cetyltransferase gene, an alkaline phosphatase gene, beta-galactosidase,a luciferase gene, a green fluorescent protein gene, guanine xanthine phosphoribosyltransferase, alkaline phosphatase, and antibiotic resistance genes (e.g., neomycin phosphotransferase).

Expression of the exogenous gene is indicative of composition-CCR5 promoter binding, thus, the binding or blocking composition can be identified and isolated. The compositions of the present invention can be extracted and purified from the culture media or a cell by using known protein purification techniques commonly employed, such as extraction, precipitation, ion exchange chromatography, affinity chromatography, gel filtration and the like. Compositions can be isolated by affinity chromatography using the modified receptor protein extracellular domain bound to a column matrix or by heparin chromatography.

In another aspect, the invention provides a method for identifying a composition which modulates the transcription activity of a CCR5 promoter polymorphism. The method includes incubating components comprising the composition and a nucleic acid sequence comprising the CCR5 promoter polymorphism operably linked to a detectable reporter under conditions sufficient to allow the components to interact; and identifying a composition which modulates CCR5 promoter polymorphism activity by detecting the reporter. The composition or compound may be provided as a library of candidate compounds. The reporter may include those described herein, such as CAT or GFP, or other common reporters known to those of skill in the art.

In a preferred embodiment, the invention provides a method for identifying a composition which modulates the transcription activity of a CCR5 promoter polymorphism. The method includes incubating components comprising the composition and a nucleic acid sequence comprising the CCR5 promoter polymorphism operably linked to a detectable reporter under conditions sufficient to allow the components to interact; and identifying a composition which modulates CCR5 promoter polymorphism activity by detecting the reporter.

The method of the invention is applicable for detection of CCR5 promoter polymorphisms. In order to analyze samples according to the method of the invention, it may desirable to amplify the target nucleic acid (i.e., CCR5 promoter) sequence before detection. This can be accomplished using oligonucleotide(s) which are primers for amplification. These unique oligonucleotide primers are based upon identification of the flanking regions contiguous with the target nucleotide sequence and are capable of substantially hybridizing with the flanking regions so that amplification can proceed. For example, in the present method, primers suitable for amplification of the target sequence include: 5'-CCCGTGAGCCCATAGTTAAAACTC-3' (SEQ ID NO:11); and 5'-TTGTATGAGCACTTGGTGTTTGCC-3' (SEQ ID NO:12) and sequences complementary thereto.

The primers which can be used according to the method of the invention embrace oligonucleotides of sufficient length and appropriate sequence so as to provide specific initiation of polymerization of a significant number of nucleic acid molecules containing the target nucleic acid. In this manner, it is possible to selectively amplify the specific target nucleic acid sequence containing the nucleic acid of interest. Specifically, the term "primer" as used herein refers to a sequence comprising two or more deoxyribonucleotides or ribonucleotides, preferably at least eight, which sequence is capable of initiating synthesis of a primer extension product, which is substantially complementary to a target nucleic acid strand. The oligonucleotide primer typically contains 15–22 or more nucleotides, although it may contain fewer nucleotides.

Experimental conditions conducive to synthesis include the presence of nucleoside triphosphates and an agent for polymerization, such as DNA polymerase, and a suitable temperature and pH. The primer is preferably single stranded for maximum efficiency in amplification but may be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition.

Primers used according to the method of the invention are designed to be "substantially" complementary to each strand of target nucleotide sequence to be amplified. Substantially complementary means that the primers must be sufficiently complementary to hybridize with their respective strands under conditions which allow the agent for polymerization to function. In other words, the primers should have sufficient complementarily with the flanking sequences to hybridize therewith and permit amplification of the nucleotide sequence. Preferably, the 3' terminus of the primer that is extended has perfectly base paired complementarity with the complementary flanking strand.

Oligonucleotide primers used according to the invention are employed in any amplification process that produces increased quantities of target nucleic acid. Typically, one primer is complementary to the negative (−) strand of the target nucleotide sequence and the other is complementary to the positive (+) strand. Annealing the primers to denatured nucleic acid followed by extension with an enzyme, such as the large fragment of DNA Polymerase I (Klenow) or Taq DNA polymerase and nucleotides results in newly synthesized + and − strands containing the target nucleic acid. Because these newly synthesized nucleic acids are also templates, repeated cycles of denaturing, primer annealing, and extension results in exponential production of the region (i.e., the target nucleotide sequence) defined by the primer. The product of the amplification reaction is a discrete nucleic acid duplex with termini corresponding to the ends of the specific primers employed. Those of skill in the art will know of other amplification methodologies which can also be utilized to increase the copy number of target nucleic acid.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

The oligonucleotide primers for use in the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters*, 22:1859–1862, 1981). One method for synthesizing oligonucleotides on a modified solid support is described in U.S. Pat. No. 4,458,066. One method of amplification which can be used according to this invention is the polymerase chain reaction (PCR) described in U.S. Pat. Nos. 4,683,202 and 4,683,195.

Any sample nucleic acid, in purified or nonpurified form, can be utilized as the starting nucleic acid or acids, provided it contains, or is suspected of containing, the CCR5 promoter sequence. Thus, the process may employ, for example, DNA wherein DNA may be single stranded or double stranded. A mixture of nucleic acids may also be employed, or the nucleic acids produced in a previous amplification reaction herein, using the same or different primers may be so utilized. The target nucleotide sequence to be amplified, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

Where the target target nucleotide sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means; the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (*CSH-Quantitative Biology,* 43:63, 1978) and techniques for using RecA are reviewed in C. Radding (*Ann. Rev. Genetics,* 16:405–437, 1982).

If the nucleic acid containing the target nucleic acid to be amplified is single stranded, its complement is synthesized by adding one or two oligonucleotide primers. If a single primer is utilized, a primer extension product is synthesized in the presence of primer, an agent for polymerization, and the four nucleoside triphosphates described below. The product will be complementary to the single-stranded nucleic acid and will hybridize with a single-stranded nucleic acid to form a duplex of unequal length strands that may then be separated into single strands to produce two single separated complementary strands. Alternatively, two primers may be added to the single-stranded nucleic acid and the reaction carried out as described.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7–9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

In some amplification embodiments, the substrates, for example, the deoxyribonucleotide triphosphates DATP, dCTP, dGTP, and dTTP, are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase I, Taq polymerase, Klenow fragment of *E. coli* DNA polymerase I, T4 DNA polymerase, other available DNA polymerases, polymerase muteins, reverse transcriptase, ligase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each target nucleotide strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above. In any event, the method of the invention is not to be limited to the embodiments of amplification which are described herein.

The newly synthesized target nucleotide strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The above process is repeated on the single-stranded molecules. Additional agent for polymerization, nucleosides, and primers may be added, if necessary, for the reaction to proceed under the conditions prescribed above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the target target nucleotide sequence to the extent necessary for detection. The amount of the target nucleotide sequence produced will accumulate in an exponential fashion.

The amplified product may be detected by analyzing it by Southern blots without using radioactive probes. In such a process, for example, a small sample of DNA containing a very low level of target nucleotide sequence is amplified, and analyzed via a Southern blotting technique. The use of non-radioactive probes or labels is facilitated by the high level of the amplified signal.

Nucleic acids having a mutation detected in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology,* (1985) 3:1008), allele-specific oligonucleotide (ASO) probe analysis (Conner, et al., *Proc. Natl. Acad. Sci. USA,* 80:278), oligonucleotide ligation assays (OLAs) (Landegren, et al., *Science,* (1988) 241:1077), and the like. Molecular techniques for DNA analysis have been reviewed (Landegren, et al., *Science,* (1988) 242:229). Thus, in a preferred embodiment where the target nucleotide sequence to be detected is a CCR5 promoter polymorphism, a hybridization probe is utilized which is capable of hybridizing with target nucleotide sequences comprising:

One method of in vitro amplification which can be used according to this invention is the polymerase chain reaction (PCR) described in U.S. Pat. Nos. 4,683,202 and 4,683,195. The term "polymerase chain reaction" refers to a method for amplifying a DNA base sequence using a heat-stable DNA polymerase and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce rapid and highly specific amplification of the desired sequence. The polymerase chain reaction is used to detect the existence of the defmed sequence in the microsatellite DNA sample. Many polymerase chain methods are known to those of skill in the art and may be used in the method of the invention. For example, DNA can be subjected to 30 to 35 cycles of amplification in a thermocycler as follows: 95° C. for 30 sec, 52° to 60° C. for 1 min, and 72° C. for 1 min, with a final extension step of 72° C. for 5 min. For another example, DNA can be subjected to 35 polymerase chain reaction cycles in a thermocycler at a denaturing temperature of 95° C. for 30 sec, followed by varying annealing temperatures ranging from 54–58° C. for 1 min, an extension step at 70° C. for 1 min and a final extension step at 70° C.

Where the target nucleic acid is not amplified, detection using an appropriate hybridization probe may be performed directly on the sample. In those instances where the target nucleic acid is amplified, detection with the appropriate hybridization probe would be performed after amplification.

For the most part, the probe will be labelled with an atom or inorganic radical, most commonly using radionuclides, but also perhaps heavy metals. Conveniently, a radioactive label may be employed. Radioactive labels include $^{32}P$, $^{125}I$, $^{3}H$, $^{14}C$, or the like. Any radioactive label may be employed which provides for an adequate signal and has sufficient half-life. Other labels include ligands, which can serve as a specific binding pair member for a labelled ligand, and the like. A wide variety of labels have been employed in immunoassays which can readily be employed in the present assay. The choice of the label will be governed by the effect of the label on the rate of hybridization and binding of the probe to target nucleotide sequence. It will be necessary that the label provide sufficient sensitivity to detect the amount of target nucleotide sequence available for hybridization. Other considerations will be ease of synthesis of the probe, readily available instrumentation, ability to automate, convenience, and the like.

The manner in which the label is bound to the probe will vary depending upon the nature of the label. For a radioactive label, a wide variety of techniques can be employed. Commonly employed is nick translation with an a $^{32}P$-DNTP or terminal labeling with radioactive $^{32}P$ employing $\gamma^{32}P$-ATP and T4 polynucleotide kinase. Alternatively, nucleotides can be synthesized where one or more of the elements present are replaced with a radioactive isotope, e.g., hydrogen with tritium. If desired, complementary labelled strands can be used as probes to enhance the concentration of hybridized label.

Where other radionuclide labels are involved, various linking groups can be employed. A terminal hydroxyl can be esterified, with inorganic acids, (e.g., $^{32}P$ phosphate), or $^{14}C$ organic acids, or else esterified to provide linking groups to the label. Alternatively, intermediate bases may be substituted with activatable linking groups which can then be linked to a label.

Enzymes of interest as reporter groups will primarily be hydrolases, particularly esterases and glycosidases, or oxidoreductases, particularly peroxidases. Fluorescent compounds include fluorescein and its derivatives, rhodamine and its derivatives, dansyl, u-mbelliferone, and so forth. Chemiluminescers include luciferin, and 2, 3-dihydrophthalazinediones (e.g., luminol).

The probe can be employed for hybridizing to a nucleotide sequence affixed to a water insoluble porous support. Depending upon the source of the nucleic acid, the manner in which the nucleic acid is affixed to the support may vary. Those of ordinary skill in the art know, or can easily ascertain, different supports which can be used in the method of the invention.

Without her elaboration, it is believed that one skilled in the art can, using the preceding description, utilize the present invention to its fullest extent. The following examples are to be considered illustrative and thus are not liniting of the remainder of the disclosure in any way whatsoever.

EXAMPLE 1

Methods for Identification of the CCR5 Promoter

Cell Culture: Derivation of human CD4+ and CD8+ tumor infiltrating T lymphocytes (Til cells) has been previously described (J. R. Yannelli, *J Immunol Meth* (1991) 139: 1; F. Liao et al., *J Exp Med* (1995) 182:1301). The cells were generously provided by J. Farber (NIAID, NIH, Bethesda, Md.). The histiocytic lymphoma cell line U937 and the acute T cell leukemia cell line Jurkat were obtained from the American Type Culture Collection (Rockville, Md.). U937 and Jurkat cells were grown in RPMI 1640 (Biofluids, Rockville, Md.) supplemented with 10% heat-inactivated fetal bovine serum (FBS; Hyclone, Logan, Utah, or Life Technologies, Gaithersburg, Md.), 2 mM glutamine, 100 units/ml penicillin, and 100 µg/ml streptomycin (Quality Biologicals, Gaithersburg, Md.). CD4 and CD8 Til cells were grown in AIM-V medium with IL-2 500 U/ml, glutamine, streptomycin 50 µg/ml and gentamicin 10 µg/ml (Life Technologies) supplemented with 10% heat-inactivated FBS. HEK 293 cells were grown in DMEM (Biofluids) supplemented with 10% FBS, 4.5 g/l glucose, 2 mM glutamine, 100 units/ml penicillin, and 100 µg/ml streptomycin. All cells were grown at 37° C. and 5% $CO_2$ in a humidified incubator.

Northern Blot Analysis of RNA: Total RNA was isolated from cultured cell lines and primary leukocytes using a kit (Qiagen, Chatsworth, Calif. or Stratagene, La Jolla, Calif.). PBMCs were purified from healthy human donors by Hypaque/Ficoll density gradient centrifugation, dextran sedimentation, and hypotonic lysis of residual erythrocytes. Lymphocytes and monocytes were separated by adherence of the mononuclear layer from the Hypaque/Ficoll gradient to tissue culture plastic in RPMI 1640 with 10% FBS at 37° C. and 5% $CO_2$ for 18 h. Lymphocytes were recovered in the non-adherent fraction of cells.

Highly purified human monocytes were obtained by elutriation performed by the Dept. of Transfusion Medicine, NIH. Isolated RNA (10 µg/lane) was electrophoresed in a 1% agarose gel containing 2% formaldehyde in MOPS buffer (pH 7.0) consisting of 10 mM MOPS, 5 mM sodium acetate and 1 mM EDTA. After migration, RNA was transferred overnight by capillary action onto Nytran membranes (Schleicher & Schuell, Keene, N.H.) and UV-cross-linked using a Stratalinker (Stratagene). Blots were probed with the total open reading frame (ORF) of CCR5 labeled with [α-$^{32}P$]dCTP using a random primed DNA labeling kit (Boehringer Mannheim, Indianapolis, Ind.), and purified on size exclusion columns (Stratagene). The blots were prehybridized in a buffer containing 50% formamide, 6×SSPE, 0.5% sodium dodecyl sulfate, 50 µg/ml denatured salmon sperm DNA for 90 min at 37° C. The radiolabelled probe was added (1×10$^6$ cpm/ml), and the filters were hybridized overnight at 37° C. The filters were then washed with 1×SSPE and 0.1% sodium dodecyl sulfate at 60° C. for 30 min and autoradiographed with Kodak X-Omat AR films between intensifying screens at −80° C.

RNA Analysis by Primer Extension: Polyadenylated RNA was purified from CD4 Til cell total RNA using the Poly(A) Quik Kit (Stratagene), and 1 μg was analyzed using a cornmercial primer extension kit according to the instructions of the manufacturer (Promega, Madison, Wis.). Briefly, an antisense CCR5-specific primer (10 pmoles), corresponding to nucleotides 78 to 58 (5'-TGGACTTGACACTTGATAATC-3', SEQ ID NO:2) of the clone 134 cDNA encoding CCR5 reported by C. J. Raport et al., *J Biol Chem* (1996) 271:17161, was end-labelled with [γ-$^{32}$P]ATP and annealed to the poly(A)+RNA at 53° C. for 20 min before reverse transcription using avian myeloblastosis virus-reverse transcriptase. A control reaction was performed in parallel using control RNA provided in the kit. The reaction products were separated on a 6% acrylamide gel containing 8 M urea along with known DNA sequence for size determination. After electrophoresis, the gel was dried and visualized by autoradiography.

Genomic DNA Analysis: CCR5 genomic clones were isolated by plaque hybridization from a commercially available human library in the vector lambda FIX (Stratagene) using the 63-2 cDNA encoding a portion of the CCR5 ORF as a probe (C. Combadiere et al., *DNA Cell Biol* (1995) 14:673), labelled with [α-$^{32}$P]dCTP by the random primed DNA labelling kit. Clones containing the 5' end of the gene were identified by hybridization with two 5'-UTR sense primers corresponding to nucleotides I to 21 (5'-AGAAGAGCTGAGACATCCGTT-3', SEQ ID NO:3) and nucleotides 18 to 42 (5'-CGTTCCCCTACAAGAAACTCTCCC-3', SEQ ID NO:4) of the clone 134 CCR5 cDNA (Raport, supra). The same probes were then used for mapping restriction sites and to identify appropriate restriction fragments for subcloning, sequencing and functional analysis. DNA sequences were analyzed with software from the University of Wisconsin Genetics Computer Group on a Cray supercomputer maintained by the National Cancer Institute Advanced Scientific Computing Laboratory, Frederick Cancer Research and Development Center, Frederick, Md. (J. Devereux et al., *Nuc Acids Res* (1984) 12:389).

Reporter Gene Constructs: The reporter gene used in these studies was bacterial chloramphenicol acetyltransferase (CAT) as found in the pCAT-basic expression vector (Promega). A 2.5 kb EcoRI/XbaI fragment containing the putative 5' end of the CCR5 gene was subcloned into Bluescript KS II. Portions of this fragment were amplified by PCR using Pfu polymerase (Stratagene) and primers containing 21 specific nucleotides with additional 5' nucleotides encoding either PstI or Xbal sites to facilitate subcloning upstream of CAT. The PCR conditions were: denaturation at 94° C. for 90 sec, annealing at 59° C. for 2 min, extension at 72° C. for 2 min, 25 cycles. All constructs were confirmed by DNA sequencing on both strands. The pCAT-basic plasmid, which contains the CAT ORF without a promoter and enhancer, was used as a negative control. pSV40 (PCAT-Promoter, Promega), which has the SV40 promoter cloned in the sense orientation upstream of CAT, was used as a positive control.

CAT Assay: The human cell lines Jurkat and U937 were grown in suspension as described above to a density of 0.5 to 1.0×10$^6$ cells/ml, and adherent HEK 293 cells were grown to subconfluency. Cells were harvested and resuspended at a density of 30×10$^6$ cells/ml in their respective complete medium. Uncut plasmid DNA (20 μg, prepared with Qiagen maxiprep kit) was used to electroporate 15×10$^6$ cells in 500 μl of complete medium with a 0.4 cm gap electroporation cuvette (Bio Rad) at 960 μFD and 250 V using a Gene Pulser (Bio Rad). The cells were then chilled on ice, added to 30 ml of complete medium and incubated for 2 d at 37° C. and 5% $CO_2$ in a humidified incubator. In addition, cells were cotransfected with 10 μg pCMV (cytomegalovirus)-β-galactosidase plasmid (Clontech, Calif.) as a control for electroporation efficiency. The level of β-galactosidase activity was determined spectrophotometrically using a β-galactosidase assay kit (Promega). CAT activity was normalized to the level of expression of this control vector. After 2 days of incubation, transfected cells were harvested by centrifugation at 1800 rpm for 5 min, washed twice with phosphate-buffered saline and resuspended in 500 μl of a buffer containing 40 mM Tris (pH 7.4), 1 mM EDTA and 150 MM NaCl. The cells were incubated 5 min at room temperature, centrifuged at 14,000 rpm for 1 min, resuspended in 100 μl of 250 mM Tris pH 7.8 and disrupted by freeze/thaw four times using dry ice and a 37° C. water bath. Cell debris was removed by a 2 min centrifugation at 14,000 rpm. A portion of the supernatant containing 50 μg of protein was incubated overnight with 250 mM Tris (pH 7.5), 9 mM acetyl Coenzyme A (Pharmacia Biotech), 0.25 μCi [$^{14}$C] chloramphenicol (DuPont NEN) in a final volume of 150 μl at 37° C. The [$^{14}$C]chloramphenicol and acetylated products were then extracted with 1 ml ethyl acetate by vortexing 30 sec. The ethyl acetate layer was removed, lyophilized, resuspended in 30 μl ethyl acetate and applied to a thin layer chromatography sheet (Baker-flex silica gel 1B, J. T. Baker Inc., Philippsburg, N.J.). Separation of acetylated and unacetylated forms was performed in a chloforn/methanol (95:5) ascending mobile phase followed by autoradiography at room temperature using a phosphor screen (Molecular Dynamics, Sunnyvale, Calif.). The radioactivity of each spot was quantitated with a PhosphorImager (Molecular Dynamics). All cell lines were transfected and analyzed on the same day for each independent experiment. The relative CAT activity in each lysate was quantitated by the following equation:

$$((A_c(A_c+U_c)/(A_b/(A_b+U_b)),$$

where A and U refer to the volume of the acetylated and unacetylated forms of chloramphenicol, respectively, and c and b refer to CAT constructs and the pBasic control plasmid, respectively.

EXAMPLE 2

Results

Identification of the 5'-UTR of CCR5 mRNA: The promoters of all known chemoattractant receptor genes are separated from the ORF by one or more large introns. Therefore to locate the CCR5 promoter, it was important to first establish the complete sequence of the 5'-UTR. To do this, we first attempted to identify a rich natural source of CCR5 mRNA for primer extension analysis. A single 3.5 kb band was detected by Northern blot hybridization analysis using a CCR5 ORF probe in RNA from elutriated monocytes, freshly isolated PBMCs, non-adherent mononuclear cells, cultured CD4+ and CD8+ Til cells and Jurkat cells but not in neutrophils. The level of CCR5 RNA was found to be the highest in the cultured Til cell samples, and CD4+ Til cell RNA was chosen for primer extension analysis. Two adjacent bands of equal intensity were identified that corresponded to products extending the CCR5 primer by 77 and 78 nucleotides, respectively. Thus, the CCR5 gene appears to have two alternative tsps. After subtracting the distance of the primer from the first codon, the length of the 5'-UTR of the longer of the two mRNAs comes to 54 nucleotides.

Structural Organization of the CCR5 Gene: The 5'-UTR sequence was used as a probe to locate the CCR5 promoter on a human genomic clone. Six genomic clones were first isolated by screening a library with an ORF probe, and three of these hybridized with two oligonucleotide probes corresponding to nucleotides 1–21 and 18–42 of the full-length mRNA sequence. One of these, designated clone 6-2a, was chosen for further analysis. A 2.7 kb XbaI/EcoRI fragment of clone 6-2a hybridized to both 5'-UTR oligonucleotide probes, and was therefore subcloned and sequenced. From the 5' end, this fragment contained 1006 bp that did not match CCR5 cDNA sequence, followed by the first 43 bp of the 5'-UTR sequence of the clone 134 CCR5 cDNA, followed by 1676 bp that did not match CCR5 cDNA sequence. The 5' end of a 2.7 kb HindIII fragment of genomic clone 6-2a overlapped with the 3' end of the XbaI/EcoRI fragment by 70 bp. From the 5' end, this fragment contained 292 bp that did not match CCR5 cDNA sequence, followed by the 3'-most 11 bp of the 5'-UTR, the complete ORF, and the 3'-UTR of the CCR5 cDNA sequence. The sequence interrupting the 5'-UTR sequence begins with the 5' dinucleotide gt and ends with the 3' dinucleotide ag, consistent with splice donor and acceptor sites. Thus, the CCR5 gene has two exons, the first containing 43 bp of the 5'-UTR, the second containing 11 bp of the 5'-UTR and the entire ORF, interrupted by a 1898 bp intron. A consensus TATA sequence is located 31 bp upstream of the tsp (FIGS. 1 and 2).

Identification of the CCR5 Promoter: This structural analysis strongly suggested that the gene region upstream of exon 1 would contain a functional promoter for CCR5. A series of chimeric reporter genes were constructed in which portions of the 1006 bp fragment upstream from exon 1 were subcloned upstream from the CAT ORF in the plasmid pCAT-basic. CAT activity was measured in the human lymphoid cell line Jurkat, the human myeloid cell line U937, and the human embryonic kidney cell line 293 transiently transfected with each of these constructs.

The longest CCR5 gene region tested (construct 1) contained 971 bp upstream from exon 1 cloned in the sense orientation upstream from CAT. This region stimulated reporter gene activity 25- and 80-fold over that observed with the pCAT-basic vector in both Jurkat and U937 cells. In contrast, the same gene region tested in the reverse orientation relative to CAT (construct 2) lacked activity in both cell lines. Together these results indicate that this 971 bp gene region contains a functional promoter element for this system.

Figure 3:
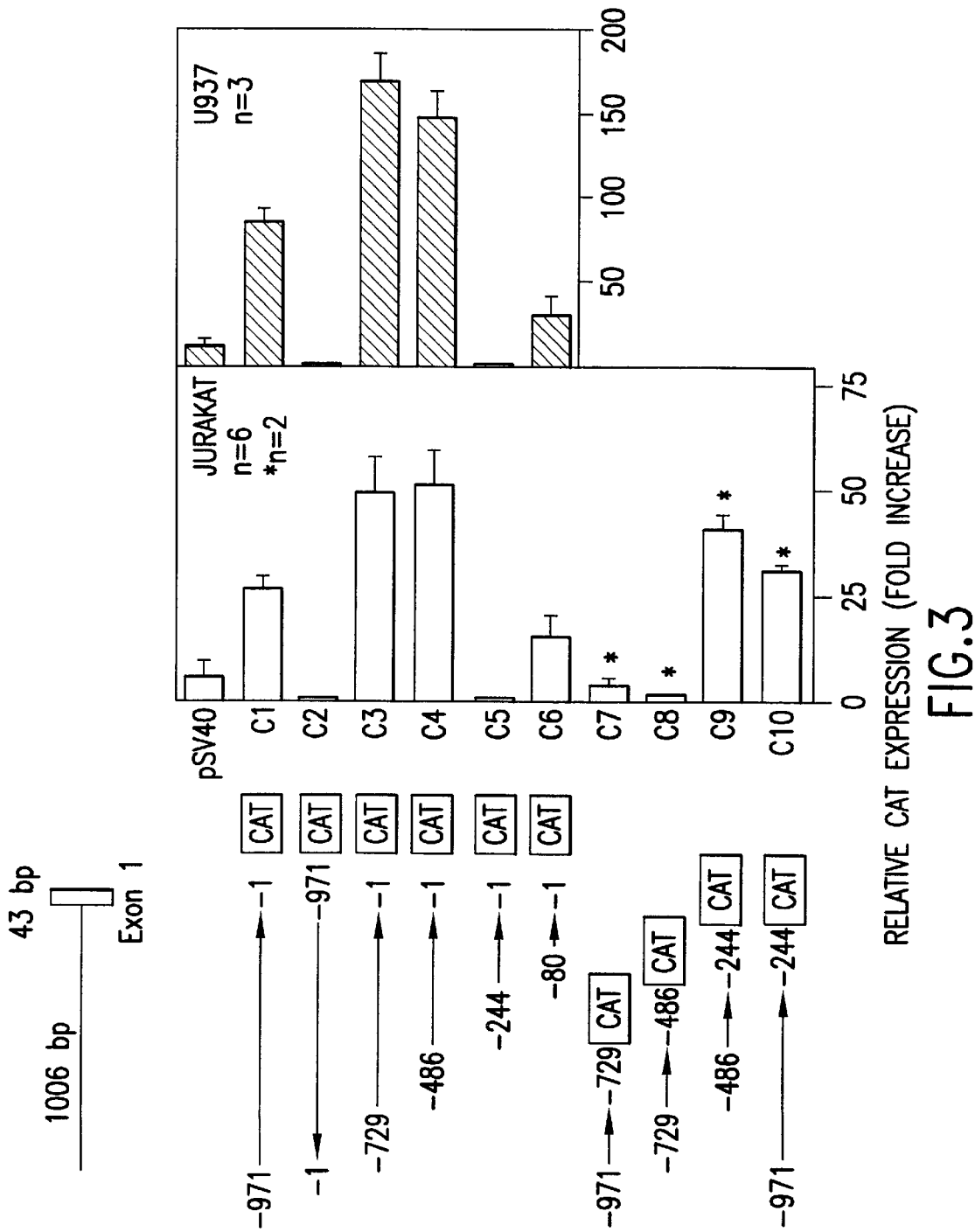
FIG. 3 shows deletional analysis of the CCR5 promoter. A construct map and data for relative CAT expression is shown. The model for the region upstream from exon 1 is shown at the upper left of the figure. The length and orientation of each gene region used for chimeric CAT constructs are indicated by arrows, with the first and last nucleotide enumerated at each end. The constructs are numbered 1–10 (C1 to C10 as indicated on the Y axis of the graph). The activity of the positive control pSV40 is indicated at the top of each graph. The CAT activity of each construct and of pSV40 relative to the negative control pCAT-basic is the mean of at least three different experiments for C1–C6 and the average of two different experiments for C7–C10. The cell type used for transfection is indicated at the upper right of each panel.

To identify a minimal promoter, a series of nested fragments were tested in the sense orientation relative to CAT containing the same 3' end as in construct 1, but having variably truncated 5' ends (constructs 3–6). Construct 6 is the shortest construct tested, only 80 bp in length. This construct retained high activity relative to construct 1, having 15 and 30-fold greater CAT activity relative to the pCAT-basic vector in Jurkat and U937 cells, respectively positive control pSV40. Thus, this gene region contains a minimal promoter in this system. Interestingly, construct 5 (−244 to −1 bp), which contains the 80 bp active region plus an additional 164 bp upstream, lacked activity in both Jurkat and U937 cells, operationally defining the presence of a silencer element in the 164 bp region in this system. Construct 4 (486 bp) contains an additional 242 bp upstream from the silencer region, which restored high promoter activity, with 50- and 140-fold increase relative to the pCAT-basic vector in the Jurkat and U937 cell lines, respectively. Thus the region from −486 to −244 appears to contain an enhancer element for this system that can silence the downstream silencer element. However, when the region from −486 to −244 was tested independently in Jurkat cells (construct 9), a 40-fold enhancement of reporter gene activity was observed, a value similar to that obtained with the longest gene region tested in construct 1. Thus, the region from −486 to −244 contains elements that can function independently as a promoter in this system (FIG. 3).

Construct 3 (nucleotides −729 to −1 relative to the tsp) contains an additional 243 bp 5' of construct 4, but had activity similar to construct 4, suggesting that the unshared gene region from −729 to −486 does not contain additional functional elements affecting reporter gene expression. Consistent with this, when this region was tested independently (construct 8), no stimulation of CAT activity was observed. Finally, the 5'-most 242 bp gene region upstream from construct 8 were tested independently and no stimulation of CAT activity was observed (construct 7, nucleotides −971 to −729). Construct 10, which tests the entire gene region tested separately in constructs 7–9, had activity similar to that observed for the gene region from −486 to −244 tested separately in construct 9. Thus the 5'-most 485 bp of the parental 971 bp gene region do not affect the constitutive promoter activity found in region −486 to −244 or in region −1 to −80.

The CCR5 promoter regions tested (constructs 1–6) also stimulated CAT expression in transiently transfected HEK 293 cells, an epithelial cell line that does not express endogenous CCR5.

Analysis of the CCR5 Sequence: When the CCR5 sequence was compared to the GenBank database using the Blast algorithm, a complete Alu repeat was identified from +1303 to +1587 relative to the tsp, placing it towards the end of the intron. In the 1006 bp region upstream from exon 1, only short stretches of limited sequence identity with other human genes, including the CXCR1 and CXCR2 promoters, were found. The CCR5 promoter region has several sequences similar to consensus sequences for the transcription factors AP-1, CCAAT-binding transcription factor/nuclear factor 1 (CTF/NF-1), NF-κB and NF-ATp, and interferon-stimulated response element (ISRE) binding protein.

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. An isolated functional CCR5 regulatory sequence consisting of nucleotide 36 to nucleotide 1006 of SEQ ID NO: 1.

2. An isolated CCR5 regulatory nucleic acid molecule consisting of nucleotides 36 to 1006 of SEQ ID NO:1, and functional portions of said nucleic acid molecule, wherein the functional portion comprises nucleotide 927 to nucleotide 1006 of SEQ ID NO: 1.

3. An isolated CCR5 regulatory nucleic acid molecule consisting of nucleotides 36 to 1006 of SEQ ID NO:1, and functional portions of said nucleic acid molecule, wherein the functional portion comprises nucleotide 521 to nucleotide 763 of SEQ ID NO: 1.

4. An isolated CCR5 regulatory nucleic acid molecule consisting of nucleotides 36 to 1006 of SEQ ID NO:1, and functional portions of said nucleic acid molecule, wherein the functional portion comprises nucleotide 763 to nucleotide 926 of SEQ ID NO:1.

5. The CCR5 regulatory sequence of claim 1, operably linked to a nucleic acid sequence encoding a heterologous protein.

6. The CCR5 regulatory sequence of claim 2, operably linked to a nucleic acid sequence encoding a heterologous protein.

7. The CCR5 regulatory sequence of claim 3, operably linked to a nucleic acid sequence encoding a heterologous protein.

8. The CCR5 regulatory sequence of claim 4, operably linked to a nucleic acid sequence encoding a heterologous protein.

9. The nucleic acid sequence of claim 5, wherein said heterologous protein comprises a cytotoxic agent.

10. The nucleic acid sequence of claim 6, wherein said heterologous protein comprises a cytotoxic agent.

11. The nucleic acid sequence of claim 7, wherein said heterologous protein comprises a cytotoxic agent.

12. The nucleic acid sequence of claim 8, wherein said heterologous protein comprises a cytotoxic agent.

13. The nucleic acid of claim 9, wherein said heterologous protein comprises an agent toxic only in the presence of a pathogen protein.

14. The nucleic acid of claim 10, wherein said heterologous protein comprises an agent toxic only in the presence of a pathogen protein.

15. The nucleic acid of claim 11, wherein said heterologous protein comprises an agent toxic only in the presence of a pathogen protein.

16. The nucleic acid of claim 12, wherein said heterologous protein comprises an agent toxic only in the presence of a pathogen protein.

17. An antisense nucleic acid sequence, comprising an oligonucleotide or oligonucleotide analog which binds to a CCR5 regulatory sequence and reduces the activity thereof, wherein said nucleic acid is a triple-helix forming agent that binds to a sequence of SEQ ID NO:1 selected from the group consisting of nucleotides 927 to 1006 of SEQ ID NO: 1 and nucleotides 521 to 763 of SEQ ID NO: 1.

18. The triple-helix forming agent of claim 17, wherein the sequence of said triple-helix forming agent comprises a sequence selected from the group consisting of:

TGTTTTTGTTTGTTGTTGTG (SEQ ID NO:5);
GTGTTGTTGTTTGTTTTTGT (SEQ ID NO:6);
TTGGTTTTGGTGTTTGTTTT (SEQ ID NO:7);
TTTTGTTTGTGGTTTTGGTT (SEQ ID NO:8);

and wherein the sequence of said triple-helix forming agent comprises a sequence of about 20 to about 38 contiguous bases taken from a sequence selected from the group consisting of:

GTTTTGTGTGTG-GTTTTTTTTGTTTTTGTTGTTGTGTGGTG (SEQ ID NO:9); and
GTGGTGTGTTGTTTTTGTTTTTTTTGGT-GTGTGTTTTG (SEQ ID NO:10).

19. A method for identifying a composition which suppresses the expression of CCR5, said method comprising:

(a) incubating the composition and the CCR5 regulatory sequence of claim 1 operably linked to a detectable reporter gene under conditions sufficient to allow the composition and CCR5 regulatory sequence to interact; and (b) identifying a composition which suppresses CCR5 regulatory region activity by selecting the composition which results in a reduction in the level of expression of the reporter gene operably linked to the CCR5 regulatory sequence in comparison to the level of reporter gene expression in the absence of said composition.

20. A method for identifying a composition which suppresses the expression of CCR5, said method comprising:

(a) incubating the composition and the CCR5 regulatory sequence of claim 2 operably linked to a detectable reporter gene under conditions sufficient to allow the composition and CCR5 regulatory sequence to interact; and (b) identifying a composition which suppresses CCR5 regulatory region activity by selecting the composition which results in a reduction in the level of expression of the reporter gene operably linked to the CCR5 regulatory sequence in comparison to the level of reporter gene expression in the absence of said composition.

21. A method for identifying a composition which suppresses the expression of CCR5, said method comprising:

(a) incubating the composition and the CCR5 regulatory sequence of claim 3 operably linked to a detectable reporter gene under conditions sufficient to allow the composition and CCR5 regulatory sequence to interact; and (b) identifying a composition which suppresses CCR5 regulatory region activity by selecting the composition which results in a reduction in the level of expression of the reporter gene operably linked to the CCR5 regulatory sequence in comparison to the level of reporter gene expression in the absence of said composition.

22. A method for identifying a composition which suppresses the expression of CCR5, said method comprising:

(a) incubating the composition and the CCR5 regulatory sequence of claim 4 operably linked to a detectable reporter gene under conditions sufficient to allow the composition and CCR5 regulatory sequence to interact; and (b) identifying a composition which suppresses CCR5 regulatory region activity by selecting the composition which results in a reduction in the level of expression of the reporter gene operably linked to the CCR5 regulatory sequence in comparison to the level of reporter gene expression in the absence of said composition.

23. The method of claim 19, wherein the reporter is selected from the group consisting of a radioisotope, a fluorescent compound, a bioluminescent compound, a chemiluminescent compound, a metal chelator, or an enzyme.

24. The method of claim 20, wherein the reporter is selected from the group consisting of a radioisotope, a fluorescent compound, a bioluminescent compound, a chemiluminescent compound, a metal chelator, or an enzyme.

25. The method of claim 21, wherein the reporter is selected from the group consisting of a radioisotope, a fluorescent compound, a bioluminescent compound, a chemiluminescent compound, a metal chelator, or an enzyme.

26. The method of claim 22, wherein the reporter is selected from the group consisting of a radioisotope, a fluorescent compound, a bioluminescent compound, a chemiluminescent compound, a metal chelator, or an enzyme.

27. The method of claim 19, wherein the reporter is a lacZ gene, a GFP gene, or a CAT gene.

28. The method of claim 20, wherein the reporter is a lacZ gene, a GFP gene, or a CAT gene.

29. The method of claim 21, wherein the reporter is a lacZ gene, a GFP gene, or a CAT gene.

30. The method of claim 22, wherein the reporter is a lacZ gene, a GFP gene, or a CAT gene.

* * * * *

SEQUENCE LISTING

<160> NUMBER OF SEQ ID NOS: 12

<210> SEQ ID NO 1
<211> LENGTH: 2961
<212> TYPE: DNA
<213> ORGANISM: Artificial Sequence
<220> FEATURE:
<223> OTHER INFORMATION: Description of Artificial Sequence:/Note = synthetic construct

<400> SEQUENCE: 1

```
tctagagcca aggtcacgga agcccagagg gcatcttgtg gctcgggagt agctctctgc      60
tgtcttctca gctctgctga caatacttga gattttcaga tgtcaccaac caccaagaga     120
gcttgatatg actgtatata gtatagtcat aaagaacctg aacttgacca tatacttatg     180
tcatgtggaa aatttctcat agcttcagat agattatatc tggagtgaag aatcctgcca     240
cctatgtatc tggcatagtg tgagtcctca taaatgctta ctggtttgaa gggcaacaaa     300
atagtgaaca gagtgaaaat ccccactaag atcctgggtc cagaaaaaga tgggaaacct     360
gtttagctca cccgtgagcc catagttaaa actctttaga caacaggttt tttccgttta     420
cagagaacaa taatattggg tggtgagcat ctgtgtgggg gttggggtgg ataggggat      480 acggggagag tggagaaaaa gggggcacag ggttaatgtg aagtccagga tccccctcta     540
catttaaagt tggtttaagt tggctttaat taatagcaac tcttaagata atcagaattt     600
tcttaacctt ttagccttac tgttgaaaag ccctgtgatc ttgtacaaat catttgcttc     660
ttggatagta atttctttta ctaaaatgtg ggcttttgac tagatgaatg taaatgttct     720
tctagctctg atatccttta ttctttatat tttctaacag attctgtgta gtgggatgag     780
cagagaacaa aaacaaaata atccagtgag aaaagcccgt aaataaactt tcagaccaga     840
gatctattct ctagcttatt ttaagctcaa cttaaaagga agaactgttc tctgattctt     900
ttcgccttca atacacttaa tgatttaact ccaccctcct tcaaaagaaa cagcatttcc     960 tactttata ctgtctatat gattgatttg cacagctcat ctggccagaa gagctgagac     1020
atccgttccc ctacaagaaa ctctcccccgg taagtaacct ctcagctgct tggcctgtta     1080
gttagcttct gagatgagta aaagacttta caggaaaccc atagaagaca tttggcaaac     1140
accaagtgct catacaatta tcttaaaata taatctttaa gataaggaaa gggtcacagt     1200
ttggaatgag tttcagacgg ttataacatc aaagatacaa aacatgattg tgagtgaaag     1260
actttaaagg gagcaatagt attttaataa ctaacaatcc ttacctctca aaagaaagat     1320
ttgcagagag atgagtctta gctgaaatct tgaaatctta tcttctgcta aggagaacta     1380
aaccctctcc agtgagatgc cttctgaata tgtgcccaca agaagttgtg tctaagtctg     1440
gttctctttt ttcttttttcc tccagacaag agggaagcct aaaaatggtc aaaattaata     1500
ttaaattaca aacgccaaat aaaattttcc tctaatatat cagtttcatg gcacagttag     1560
tatataattc tttatggttc aaaattaaaa atgagctttt ctaggggctt ctctcagctg     1620
cctagtctaa ggtgcaggga gtttgagact cacagggttt aataagagaa aattctcagc     1680
tagagcagct gaacttaaat agactaggca agacagctgg ttataagact aaactaccca     1740
gaatgcatga cattcatctg tggtggcaga cgaaacattt tttattatat tatttcttgg     1800
gtatgtatga caactcttaa ttgtggcaac tcaaactaca aacacaaact tcacagaaaa     1860
tgtgaggatt ttacaattgg ctgttgtcat ctatgacctt ccctgggact tgggcacccg     1920
```

-continued

```
gccatttcac tctgactaca tcatgtcacc aaacatctga tggtcttgcc tttaattct    1980 cttttttgagg actgagaggg agggtagcat ggtagttaag agtgcaggct tcccgcattc    2040
aaaatcggtt gcttactagc tgtgtggctt tgagcaagtt actcaccctc tctgtgcttc    2100
aaggtccttg tctgcaaaat gtgaaaaata tttcctgcct cataaggttg ccctaaggat    2160
taaatgaatg aatgggtatg atgcttagaa cagtgattgg catccagtat gtgccctcga    2220
ggcctcttaa ttattactgg cttgctcata gtgcatgttc tttgtgggct aactctagcg    2280
tcaataaaaa tgttaagact gagttgcagc tgggcatggt ggctcatgcc tgtaatccca    2340
gcattctagg aggctgaggc aggaggatcg cttgagccca ggagttcgag accagcctgg    2400
gcaacatagt gtgatcttgt atctataaaa ataaacaaaa ttagcttggt gtggtggcgc    2460
ctgtagtccc cagccacttg gagggtgag gtgagaggat tgcttgagcc cgggatgatc     2520
caggctgcag tgagccatga tcgtgccact gcactccagc ctgggcgaca gagtgagacc    2580
ctgtctccaa acaacaacag caacaaaaag gctgagctgc accatgcttg acccagtttc    2640
ttaaaattgt tgtcaaagct tcattcactc catggtgcta tagagcacaa gatttatt     2700 ggtgagatgg tgctttcatg aattcccca acagagccaa gctctccatc tagtggacag     2760
ggaagctagc agcaaacctt cccttcacta caaaacttca ttgcttggcc aaaaagagag    2820
ttaattcaat gtagacatct atgtaggcaa ttaaaaacct attgatgtat aaaacagttt    2880
gcattcatgg agggcaacta aatacattct aggactttat aaaagatcac tttttattta    2940
tgcacagggt ggaacaagat g                                              2961
```

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 2
tggacttgac acttgataat c                                                21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 3
agaagagctg agacatccgt t                                                21

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 4
cgttccccta caagaaactc tccc                                             24

<210> SEQ ID NO 5
<211> LENGTH: 20
<212> TYPE: DNA

```
<213> ORGANISM: Artificial Sequence
<220> FEATURE:
<223> OTHER INFORMATION: Description of Artificial Sequence:/Note =
      synthetic construct

<400> SEQUENCE: 5
tgtttttgtt tgttgttgtg                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 6
gtgttgttgt ttgttttttgt                                                   20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 7
ttggttttgg tgtttgtttt                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 8
ttttgtttgt ggttttggtt                                                    20

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 9
gttttgtgtg tggttttttt tgtttttgtt gtgtggtg                                38

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 10
gtggtgtgtt gttttttgttt ttttggtgt gtgttttg                                38

<210> SEQ ID NO 11
<211> LENGTH: 24
<212> TYPE: DNA
<213> ORGANISM: Artificial Sequence
```

-continued

```
<220> FEATURE:
<223> OTHER INFORMATION: Description of Artificial Sequence:/Note =
      synthetic construct

<400> SEQUENCE: 11
cccgtgagcc catagttaaa actc                                           24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 12
ttgtatgagc acttggtgtt tgcc                                           24
```